US010271858B2

(12) United States Patent
Guilloux et al.

(10) Patent No.: US 10,271,858 B2
(45) Date of Patent: Apr. 30, 2019

(54) PATIENT-SPECIFIC BONE GRAFTING SYSTEM AND METHOD

(71) Applicant: ZIMMER, INC., Warsaw, IN (US)

(72) Inventors: Sebastien Guilloux, Saint-Priest (FR); Olivier Boisvert, Montreal (CA); Karine Dupuis, Montreal (CA); Anselm Neurohr, Montreal (CA); Jean-Guillaume Abiven, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 316 days.

(21) Appl. No.: 15/167,565

(22) Filed: May 27, 2016

(65) Prior Publication Data

US 2016/0345987 A1    Dec. 1, 2016

Related U.S. Application Data

(60) Provisional application No. 62/167,686, filed on May 28, 2015.

(51) Int. Cl.
*A61B 17/16* (2006.01)
*A61B 17/17* (2006.01)
(Continued)

(52) U.S. Cl.
CPC .......... *A61B 17/1635* (2013.01); *A61B 17/15* (2013.01); *A61B 17/1637* (2013.01);
(Continued)

(58) Field of Classification Search
CPC ....... A61B 17/15; A61B 17/151; A61B 17/16; A61B 17/1635; A61B 17/1684;
(Continued)

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Tornier, Bio-RSA, Bony Increased Offset-Reversed Shoulder Arthroplasty, Surgical Technique, CAW-2150 REV B ECN 160311 Feb. 12, 2016, © 2016 Wright Medical Group N.V. or its affiliates.
(Continued)

*Primary Examiner* — Christian Sevilla
(74) *Attorney, Agent, or Firm* — Norton Rose Fulbright Canada LLP

(57) ABSTRACT

A system for generating a model of a patient specific cut guide instrument for harvesting a graft comprises a model of a graft defined by an implant interface surface, a bone interface surface, and a spatial geometry therebetween, the model being specific to a patient. A patient-specific instrument generator outputs the model of the patient specific cut guide instrument, the patient-specific instrument generator including a position determination module for orienting and positioning at least a first guide axis, and for positioning an abutment on a model of a donor bone as a function of the spatial geometry, and an instrument body generator module for generating a model of the patient specific cut guide instrument comprising a body supporting a cut guide to perform a depth cut in the donor bone positioned and oriented as a function of a contact of the body with the abutment on the donor bone, and of the model of the graft, a first guide channel for alignment with the first guide axis, and at least one anchor guide for securing the patient specific
(Continued)

instrument cut guide on the donor bone as abutted with the abutment and aligned with the first guide axis, whereby the patient specific cut guide instrument is used for harvesting the graft for subsequent implanting without alterations to the spatial geometry of the graft.

42 Claims, 29 Drawing Sheets

(51) Int. Cl.
   *A61B 17/15* (2006.01)
   *A61F 2/46* (2006.01)
   *A61B 34/10* (2016.01)

(52) U.S. Cl.
   CPC ...... *A61B 17/1684* (2013.01); *A61B 17/1778* (2016.11); *A61F 2/4612* (2013.01); *A61B 2017/1602* (2013.01); *A61B 2034/108* (2016.02)

(58) Field of Classification Search
   CPC . A61B 17/17; A61B 17/1739; A61B 17/1778; A61B 2034/108; A61F 2002/2835; A61F 2002/2853; A61F 2/4081; A61F 2/4603; A61F 2/4612; A61F 2/4644
   See application file for complete search history.

(56) References Cited

U.S. PATENT DOCUMENTS

| | | | |
|---|---|---|---|
| 5,490,854 A | 2/1996 | Fisher et al. | |
| 5,722,977 A | 3/1998 | Wilhelmy | |
| 5,768,134 A | 6/1998 | Swaelens et al. | |
| 5,871,018 A | 2/1999 | Delp et al. | |
| 5,916,219 A | 6/1999 | Matsuno et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 8,864,834 B2 * | 10/2014 | Boileau | A61B 17/1778 606/79 |
| 2003/0055502 A1 | 3/2003 | Lang et al. | |
| 2003/0216669 A1 | 11/2003 | Lang et al. | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0234461 A1 | 10/2005 | Burdulis et al. | |
| 2005/0267584 A1 | 12/2005 | Burdulis et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |

(56) References Cited

U.S. PATENT DOCUMENTS

| | | |
|---|---|---|
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1 | 4/2010 | Keefer |
| 2010/0087829 A1 | 4/2010 | Metzger et al. |
| 2010/0087927 A1 | 4/2010 | Roche et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0125003 A1 | 5/2011 | Reach ............... 600/407 |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0253350 A1* | 10/2012 | Anthony ............... A61B 17/14 606/87 |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0079781 A1 | 3/2013 | Fitz et al. |
| 2013/0079876 A1 | 3/2013 | Fitz et al. |
| 2013/0081247 A1 | 4/2013 | Fitz et al. |

(56) References Cited

U.S. PATENT DOCUMENTS

| | | |
|---|---|---|
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |
| 2013/0191085 A1 | 7/2013 | Li et al. ........................... 703/1 |
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2014/0343554 A1 | 11/2014 | Warnock |
| 2015/0012104 A1 | 1/2015 | Boileau et al. ............ 623/19.13 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 1555962 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1 952 788 A1 | 8/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |

(56) References Cited

FOREIGN PATENT DOCUMENTS

| | | | |
|---|---|---|---|
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2013177389 A1 | 11/2013 |
| WO | 2014008444 A1 | 1/2014 |
| WO | 2014035991 A1 | 3/2014 |
| WO | 2014047514 A1 | 3/2014 |
| WO | WO/15/175397 | 11/2015 |

OTHER PUBLICATIONS

Taylor et al, "Computer-Integrated Surgery, Technology and Clinical Applications", The MIT Press, Cambridge, MA, London, UK, pp. 451-463, 1995.

Hofmann et al, "Natural-Knee II System", Intermedics Orthopedics, Austin, TX, 1995.

* cited by examiner

Fig_1

Fig_14

PATIENT-SPECIFIC BONE GRAFTING SYSTEM AND METHOD

CROSS-REFERENCE TO RELATED APPLICATION

The present application claims the priority of U.S. Provisional Patent Application No. 62/167,686, filed on May 28, 2015, and incorporated herein by reference.

TECHNICAL FIELD

The present application relates to orthopedic shoulder surgery and more particularly to patient-specific instrumentation used to harvest bone grant and implant same. For example, the system and method may be applied to reverse shoulder arthroplasty, featuring humeral bone graft for eroded glenoids.

BACKGROUND OF THE ART

Bone grafts are occasionally used in orthopedic surgery. Bone grafts are used to fill gaps between a recipient bone and an implant. Bone autografts have the ability to be osteoinductive, osteogenic, and/or osteoconductive and therefore are an advantageous choice for orthopedic surgery, to interface off-the-shelf implants to bone. Allografts are also commonly used.

For example, in reverse shoulder arthroplasty, the shoulder joint involves implants that replicate the native shoulder joint, but in a reverse arrangement with the scapula forming the joint head, and the humerus forming the socket. Reverse shoulder arthroplasty is often used because of glenoid deformities and/or rotators cuff malfunction. Considering that the humerus must be machined and converted into a socket, there is a source of graft that can be used to correct glenoid deformities, and/or to create an interface between an implant and the glenoid. Humerus bone grafts may be harvested to compensate the bone loss due to glenoid erosion. As subchondral bone has been shown to be effective in stabilizing glenoid implants more than cancellous bone, it is desirable to harvest grafts in the humerus.

However, grafting techniques involving for example autografts commonly involve some graft adaptation steps, e.g., machining, alterations, for the graft to have a desired geometry for subsequent implantation. However, such machining steps may add time to a surgical procedure.

SUMMARY

It is an aim of the present disclosure to provide a method for harvesting a graft that addresses issues related to the prior art.

It is a further aim of the present disclosure that the method for harvesting a graft be used to harvest humeral bone grafts for reverse shoulder arthroplasty.

It is a still further aim of the present disclosure to provide patient-specific instruments for harvesting bone grafts for subsequent implantation.

It is a still further aim of the present disclosure that the patient-specific instruments be used in reverse shoulder arthroplasty.

Therefore, in accordance with a first embodiment of the present disclosure, there is provided a method for harvesting a graft having at least an implant interface surface, a bone interface surface, and a planned spatial geometry therebetween, the method comprising: obtaining a cut guide instrument specific to a patient's anatomy; resurfacing an exposed surface of a donor bone to form one of an implant interface surface and a bone interface surface of the graft; securing the cut guide instrument to the bone relative to resurfaced exposed surface; performing a depth cut in the donor bone to form the other of the implant interface surface and the bone interface surface of the graft with the planned spatial geometry; and harvesting the graft from the donor bone.

Further in accordance with the first embodiment, resurfacing the exposed surface of the donor bone in some instances comprises resurfacing the exposed surface to form a planar surface used as the implant interface surface.

Still further in accordance with the first embodiment, performing the depth cut in some instances comprises forming the bone interface surface into another planar surface, the exposed surface being non parallel to the bone interface surface.

Still further in accordance with the first embodiment, harvesting the graft in some instances comprises forming a cylindrical body between the implant interface surface and the bone interface surface, an axis of the cylindrical body being normal to the implant interface surface.

Still further in accordance with the first embodiment, harvesting the bone in some instances comprises securing an implant against the implant interface surface and removing the implant and graft from the donor bone.

Still further in accordance with the first embodiment, harvesting the graft in some instances comprises harvesting the graft to obtain the spatial geometry based on one of the Walch glenoid indication and Favard glenoid indication in a reverse shoulder arthroplasty.

Still further in accordance with the first embodiment, harvesting the graft in some instances comprises harvesting the graft from a humerus being the donor bone, and further comprising implanting the graft and an implant onto the glenoid in reverse shoulder arthroplasty.

Still further in accordance with the first embodiment, the graft in some instances is implanted onto a recipient bone without further alterations to the graft after said harvesting from the donor bone.

Still further in accordance with the first embodiment, resurfacing the exposed surface in some instances comprises installing a guide rod and moving a resurfacing tool on the guide rod.

Still further in accordance with the first embodiment, securing the cut guide instrument on the bone in some instances comprises sliding the cut guide instrument along the guide rod and into abutment with the exposed surface.

Still further in accordance with the first embodiment, a peg bore in some instances is formed in the graft, the peg bore being coaxial with a hole in the donor bone made by insertion of the guide rod.

Still further in accordance with the first embodiment, forming the peg bore in some instances is removing the guide rod.

Still further in accordance with the first embodiment, resurfacing the exposed surface of the donor bone in some instances comprises resurfacing the exposed surface to form a spherical surface portion used as the bone interface surface.

Still further in accordance with the first embodiment, performing the depth cut in some instances comprises forming the implant interface surface into a planar surface.

Still further in accordance with the first embodiment, harvesting the graft in some instances comprises forming a cylindrical body between the implant interface surface and the bone interface surface, an axis of the cylindrical body being normal to the implant interface surface.

Still further in accordance with the first embodiment, resurfacing the exposed surface in some instances comprises installing a first guide rod on the donor bone, and moving a resurfacing tool on the first guide rod to form said spherical surface portion.

Still further in accordance with the first embodiment, securing the cut guide instrument on the bone in some instances comprises sliding the cut guide instrument along the first guide rod and into abutment with the resurfaced exposed surface.

Still further in accordance with the first embodiment, harvesting the graft in some instances comprises installing a second guide rod with a second guide channel of the cut guide instrument on the donor bone and sliding an instrument on the second guide rod.

Still further in accordance with the first embodiment, harvesting the graft in some instances comprises forming a peg bore in the graft, the peg bore being coaxial with a hole in the donor bone made by insertion of the second guide rod.

Still further in accordance with the first embodiment, forming the peg bore in some instances is removing the second guide rod.

Still further in accordance with the first embodiment, a patient specific alignment instrument in some instances has a receptacle receiving and conforming to the bone interface surface and a hole in the receptacle receiving and aligned with the peg bore to install the implant onto the graft.

Still further in accordance with the first embodiment, the method in some instances further comprises sliding the patient specific alignment instrument along a guide pin to position and impact the implant and graft on the recipient bone.

In accordance with a second embodiment of the present disclosure, there is provided a system for generating a model of a patient specific cut guide instrument for harvesting a graft, comprising: a model of a graft defined by an implant interface surface, a bone interface surface, and a spatial geometry therebetween, the model being specific to a patient; a patient-specific instrument generator for outputting the model of the patient specific cut guide instrument, the patient-specific instrument generator including a position determination module configured to orient and position at least a first guide axis, and to position an abutment on a model of a donor bone as a function of the spatial geometry, and an instrument body generator module configured to generate a model of the patient specific cut guide instrument comprising a body supporting a cut guide to perform a depth cut in the donor bone positioned and oriented as a function of a contact of the body with the abutment on the donor bone, and of the model of the graft, a first guide portion for alignment with the first guide axis, and at least one anchor guide for securing the patient specific instrument cut guide on the donor bone as abutted with the abutment and aligned with the first guide axis, whereby the patient specific cut guide instrument is configured to be used for harvesting the graft for subsequent implanting without alterations to the spatial geometry of the graft.

Further in accordance with the second embodiment, the patient-specific instrument generator in some instances further comprises a tool selector module for identifying at least one bone-altering tool to be used for at least one of resurfacing the donor bone and harvesting the graft.

Still further in accordance with the second embodiment, the position determination module in some instances is further configured to determine a resurfacing of the donor bone to define the abutment, the resurfacing being to form a planar surface used as the implant interface surface.

Still further in accordance with the second embodiment, the instrument body generator module in some instances is further configured to orient the cut guide in the body to form the bone interface surface into another planar surface, the exposed surface being non parallel to the bone interface surface.

Still further in accordance with the second embodiment, the tool selector module in some instances is further configured to identify a bell saw to harvest the graft by forming a cylindrical body between the implant interface surface and the bone interface surface, an axis of the cylindrical body being normal to the implant interface surface.

Still further in accordance with the second embodiment, the instrument body generator module in some instances is further configured to generate the model of the patient specific cut guide instrument based on one of the Walch glenoid indication and Favard glenoid indication in a reverse shoulder arthroplasty.

Still further in accordance with the second embodiment, a humerus in some instances is the donor bone, and the graft is configured to be used to support an implant onto the glenoid in reverse shoulder arthroplasty.

Still further in accordance with the second embodiment, the guide portion in some instances is a guide channel sized to be used with a guide rod at the first guide axis.

Still further in accordance with the second embodiment, the tool selector module in some instances is further configured to select tools that are configured to slide along the guide rod and into contact with the abutment.

Still further in accordance with the second embodiment, the instrument body generator module in some instances is further configured to define a hole in the body, the hole being sized as a function of a peg bore to be formed in the graft, the peg bore being coaxial with a hole in the donor bone made by insertion of the guide rod.

Still further in accordance with the second embodiment, the position determination module in some instances is further configured to determine a resurfacing of the donor bone to define the abutment, the resurfacing being to form a spherical surface portion used as the bone interface surface.

Still further in accordance with the second embodiment, the instrument body generator module in some instances is further configured to orient the cut guide in the body to form the implant interface surface into a planar surface.

Still further in accordance with the second embodiment, the position determination module in some instances is further configured to orient and position a second guide axis on the donor bone, the tool selector module identifies a bell saw to move along the second guide axis to harvest the graft by forming a cylindrical body between the implant interface surface and the bone interface surface, an axis of the cylindrical body being normal to the implant interface surface.

Still further in accordance with the second embodiment, the instrument body generator module in some instances is further configured to generate a model of a patient specific alignment instrument having a receptacle receiving and conforming to the bone interface surface and a hole in the receptacle receiving and aligned with a peg bore coincident with a hole along the second guide axis, to install the implant onto the graft.

Still further in accordance with the second embodiment, the patient specific alignment instrument in some instances further comprises a guide pin and channel assembly to position and impact the implant and graft on the recipient bone.

Still further in accordance with the second embodiment, the tool selector module in some instances is further configured to select a resurfacing tool to move along a first guide rod coincident with the first guide axis on the donor bone for resurfacing the exposed surface into said spherical surface portion.

Still further in accordance with the second embodiment, the patient specific cut guide instrument for creating the graft in some instances comprises a model file including a spatial model of a graft defined by an implant interface surface and a bone interface surface of the graft and a spacing therebetween; the body including a baseplate adapted to be abutted against the abutment, the cut guide adapted to receive therein a cut blade, and at least one depth leg spacing the base plate away from the cut guide; wherein the base plate, the cut guide slot and the at least one depth leg replicate parameters of the spatial model of the graft.

The feature or features of one embodiment may be applied to other embodiments, even though not described or illustrated, unless expressly prohibited by this disclosure or the nature of the embodiments.

Some details associated with the present embodiments are described above and others are described below.

DETAILED DESCRIPTION

Figure 1:
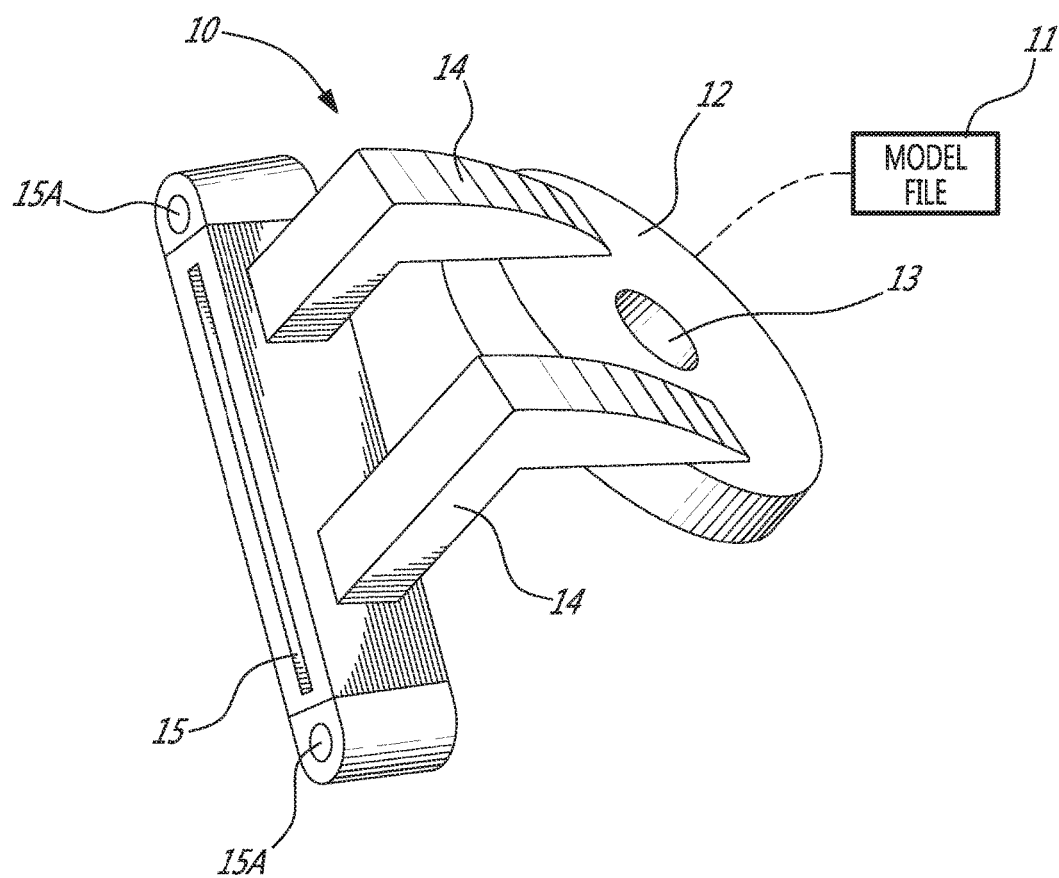
FIG. 1 is a perspective view of a humerus grafting patient-specific instrument in accordance with a first embodiment of the present disclosure.

Referring to the drawings, methods for harvesting a graft is generally shown. The illustrated methods show the harvesting of a graft on the humerus in a reverse shoulder arthroplasty, for example in an autograft or allograft situation (including a cadaver allograft). However, the methods may apply to other bones as well, for example using the iliac crest as a donor bone. For simplicity, the examples of the present disclosure focus on a reverse shoulder arthroplasty with the humerus as donor bone, although other bones could be used in accordance with the present disclosure.

In FIG. 1, a humerus grafting patient-specific instrument is generally shown at 10. The humerus grafting patient-specific instrument 10 is said to be patient-specific, in that its geometry is modeled based on a planning for every patient's unique anatomy, using imaging techniques. Stated differently, the humerus grafting patient-specific instrument 10 is developed subsequent to pre-operative steps by which a patient's anatomy is modeled and the implant position is defined. Hence, the humerus grafting patient-specific instrument 10 has an identity related to a patient, and is most likely inadequate for being used with other patients, whereby the instrument 10 is typically a one-time use instrument. Accordingly, the humerus grafting patient-specific instrument 10 has a model file 11 of non-transient format which features a two-dimensional or three-dimensional model of the patient's anatomy resulting from pre-operative imaging. The specific geometry of the components of the humerus grafting patient-specific instrument 10 are directly related to the contents of the model file 11.

The humerus grafting patient-specific instruments of the present disclosure are designed to carve out a graft in the native humerus (e.g., especially in autograft procedure, but also in allograft), which humerus graft will be used as an interface between a glenoid cavity and an implant. The humerus is therefore in this example the donor bone, whereas the scapula is the receiver bone. Accordingly, the model file 11 may define a specific spatial geometry for the humerus graft, featuring a glenoid interface surface that will lie against the reamed glenoid, an implant interface surface against which an undersurface of the implant will lie, and lateral wall(s) between the glenoid interface surface and the implant interface surface. The humerus grafting patient-specific instruments and methods described herein are such that little or no machining steps are required on the humeral graft once harvested. Indeed, some prior art techniques suggest removing a voluminous humeral graft, to then suggest the machining of the graft prior to grafting. The PSI technique taught herein allows the surgeon to plan the implant position with a graft, while execution is intraoperative.

Figure 2:
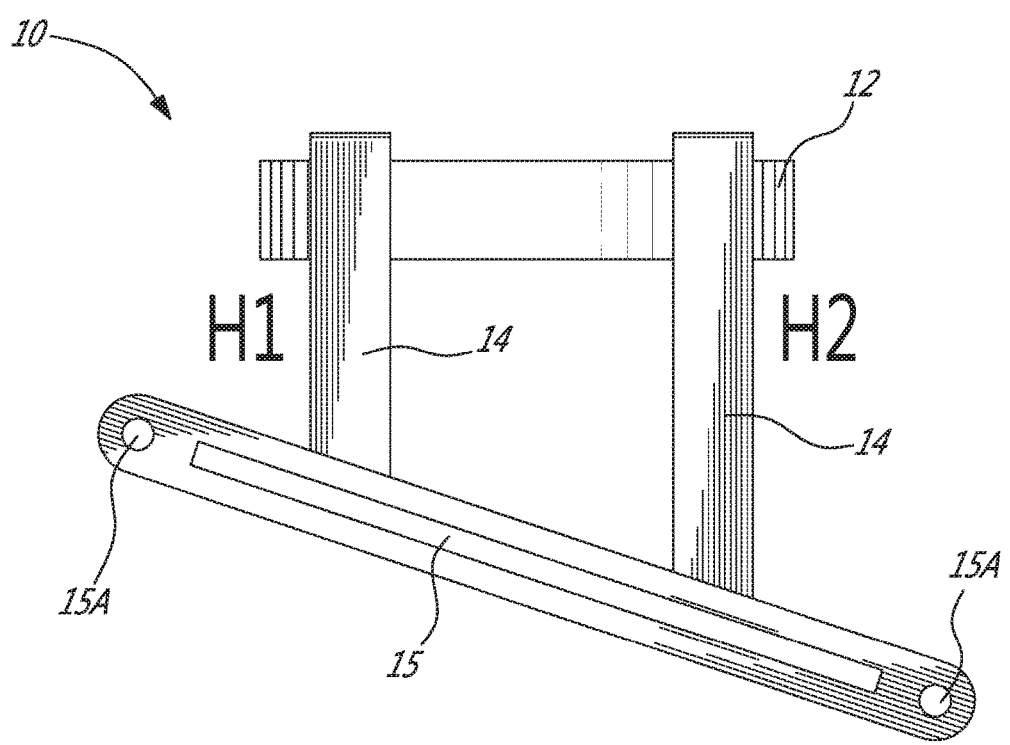
FIG. 2 is a schematic side view of the humerus grafting patient-specific instrument of FIG. 1.
Figure 3:
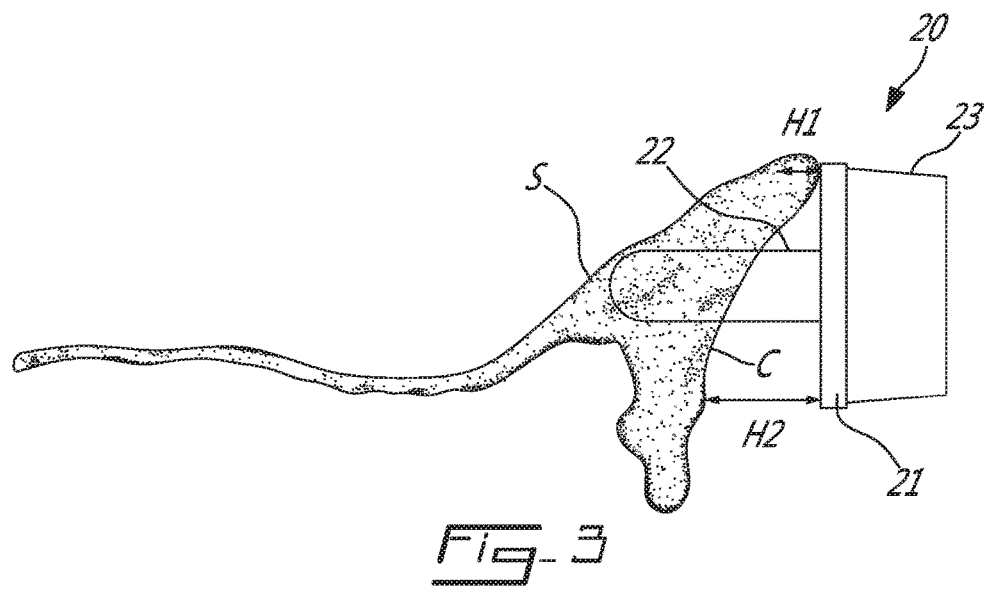
FIG. 3 is a transverse view showing a planned positioning of a glenoid implant relative to a scapula.
Figure 4:
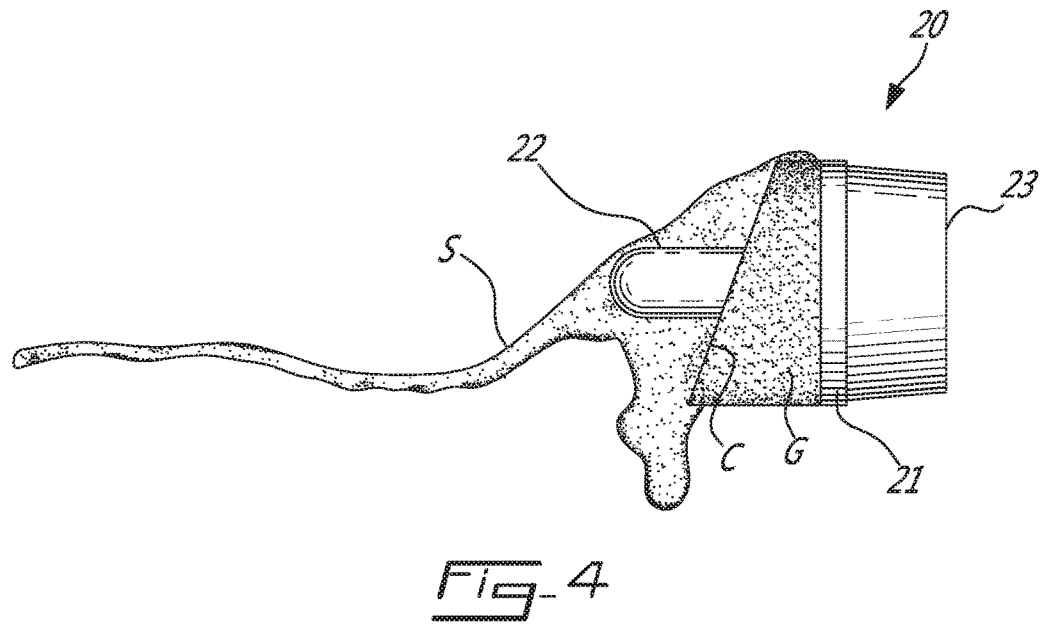
FIG. 4 is the transverse view of FIG. 3, with a humerus graft positioned between the glenoid implant and the reamed glenoid.

Referring to FIG. 1, the instrument 10 is shown as having a base plate 12. The base plate 12 is shown as being generally circular (i.e., disc-shaped) but other shapes are considered as well. A guide bore 13 is provided through the base plate 12 and will be used as described hereinafter as a guide for translational/rotational movements. One or more depths legs 14 project from the base plate 12 and support a cut slot 15—with pin guides 15A—at ends opposite to the base plate 12. The cut slot 15 is configured to receive a cut blade therein. As shown in FIG. 2, the length of the depth legs 14 is illustrated as H1 and H2 (determined using the surgeon planning of the implant relative to the glenoid). With reference to FIG. 3, it is shown that H1 and H2 may be representative of two distinct dimensions between a glenoid implant 20 and a glenoid cavity C, the glenoid implant 20 shown as having a base plate 21 and a peg 22. The base plate 21 is optional in the implant 20, and supports a tapered head 23 that will be part of the shoulder joint. The H1 and H2 dimensions are based on a planning indication known as Walch glenoid indication, in which the glenoid cavity is reamed into a plane without sacrificing excessively the glenoid cavity surface. H1 and H2 are representative of the spacing between the base plate 21 and the reamed glenoid cavity C (i.e., the recipient site or location) as shown in FIG. 4, whereby the harvesting of graft should have dimensions H1 and H2 to replicate the assembly shown in FIG. 4. The positioning of the glenoid implant 20 also takes into consideration a depth of insertion of the peg 22 in the shoulder blade S. Accordingly, the humerus grafting patient-specific instrument 10 is devised so as to harvest humerus graft G of FIG. 4.

Figure 5:
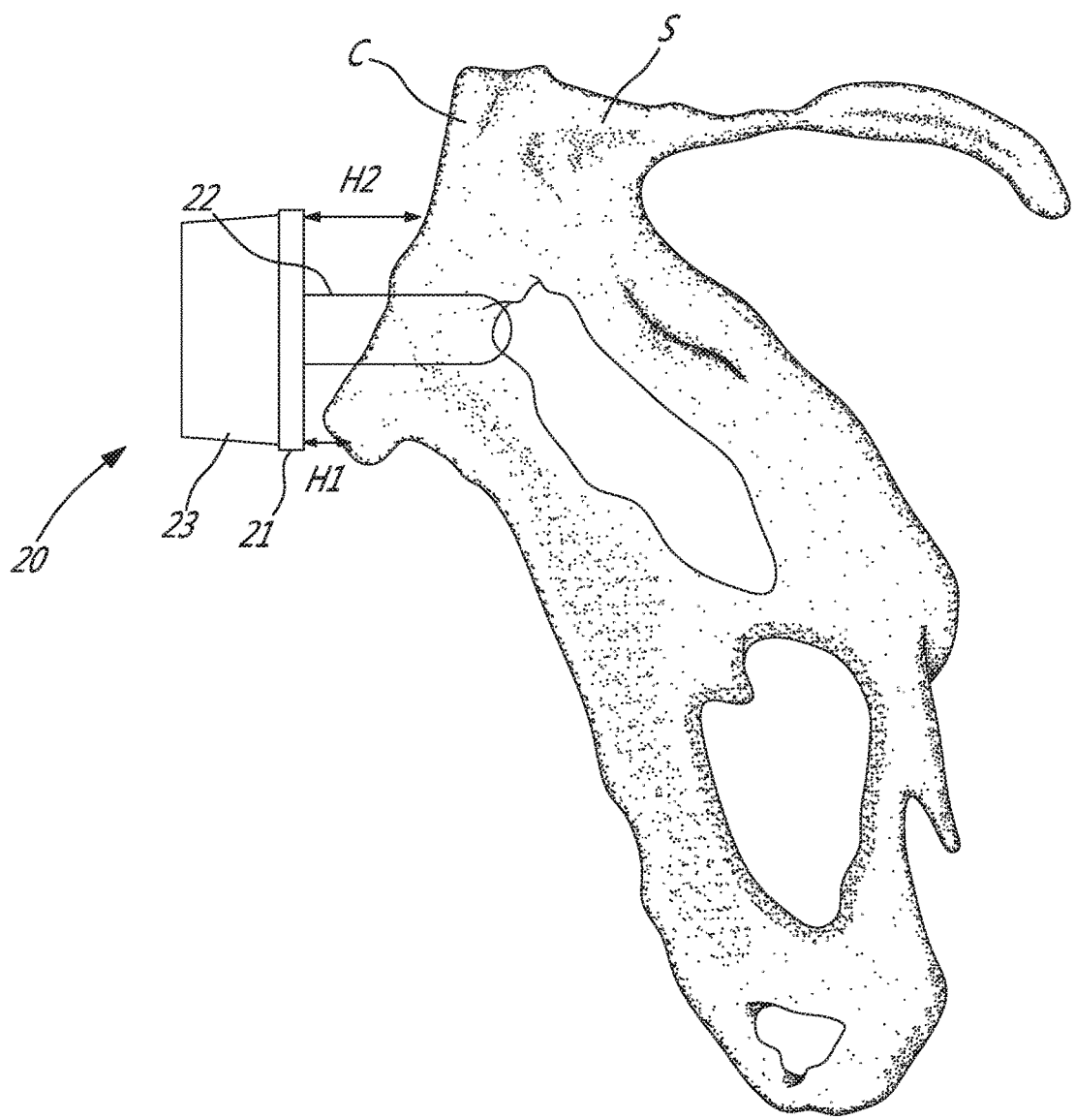
FIG. 5 is a frontal view of a glenoid implant relative to a scapula in another embodiment.
Figure 6:
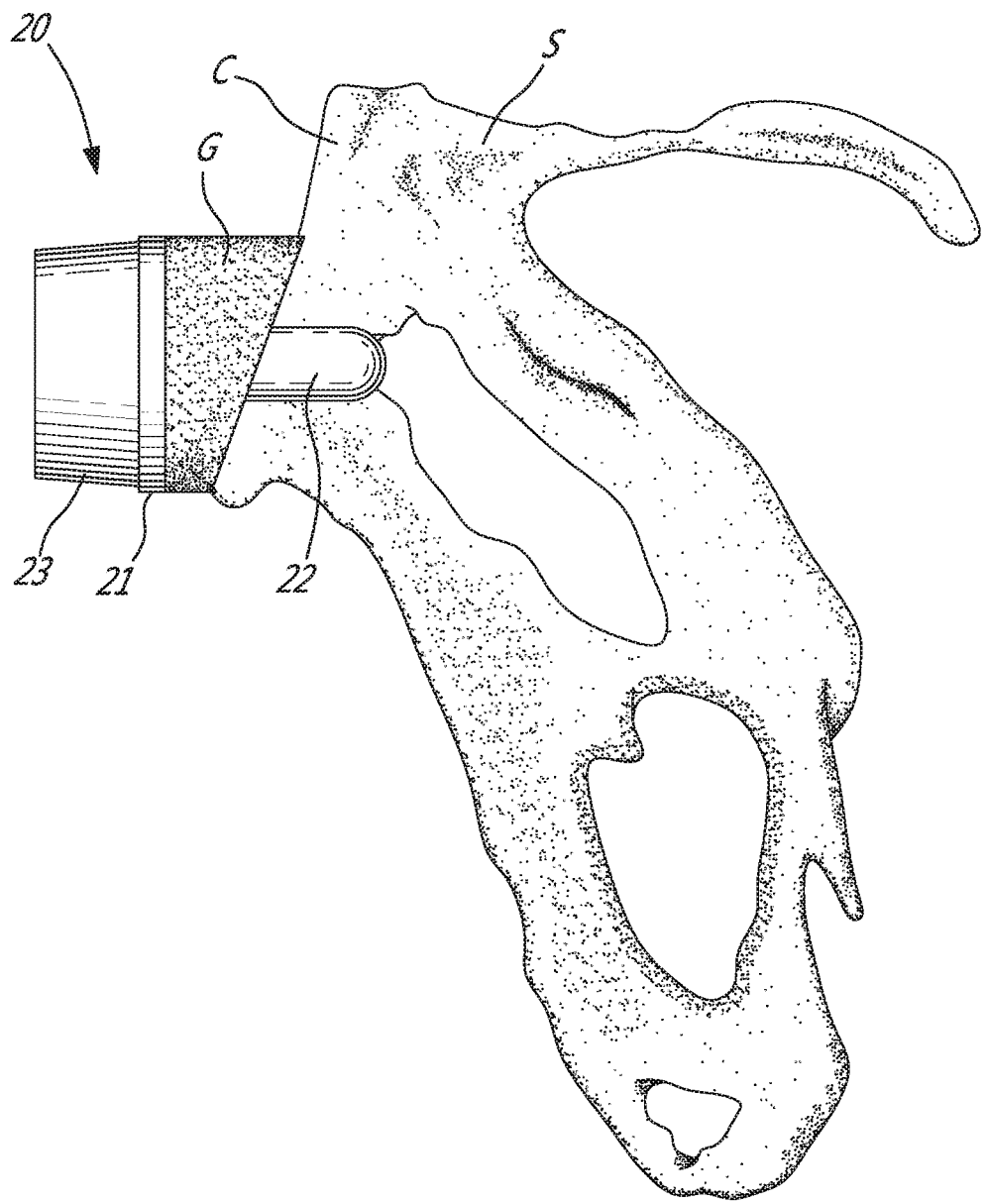
FIG. 6 is a frontal view of the glenoid implant and scapula of FIG. 5, with a humerus graft in the reamed glenoid.

Alternatively, the assessment of H1 and H2 may be based on a Favard glenoid indication as shown in FIGS. 5 and 6. Whether the glenoid implanting is based on the Walch glenoid indication, the Favard glenoid indication or other implanting in which the glenoid surface is planar, the instrument 10 will be similar with, however, an adjustment of the length of the depth legs 14 as per dimensions H1 and H2, dependent on which of the indications will be used in the planning stages of surgery.

With the instrument 10 being created in pre-operative planning, a method for harvesting the humerus graft G may be performed using the instrument 10, as described hereinafter.

Figure 7:
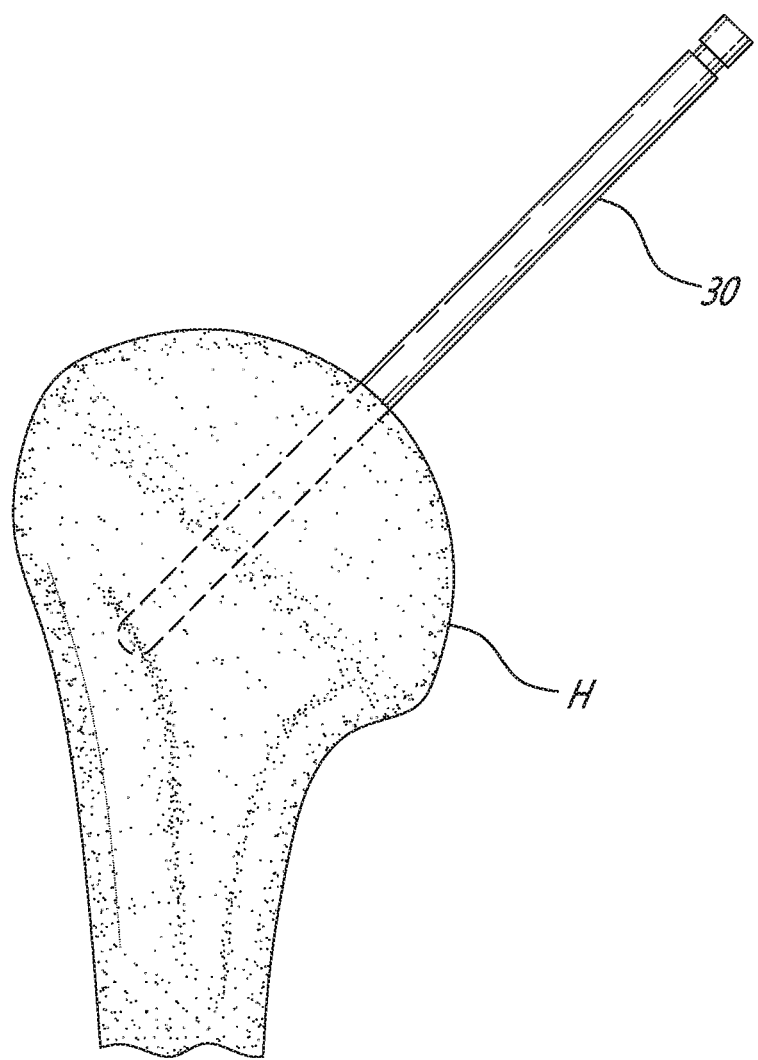
FIG. 7 is a schematic view demonstrating a humerus with a guide rod.

In FIG. 7, a guide rod 30 is positioned in the humerus H in preparing for the humerus grafting. Although not shown, the positioning of the guide rod 30 may result from the use of different pins and drills to properly orient the guide rod 30, to a desired depth. Other patient-specific instruments may be used to properly orient the guide rod 30, or other technologies such as inertial sensors.

Figure 8:
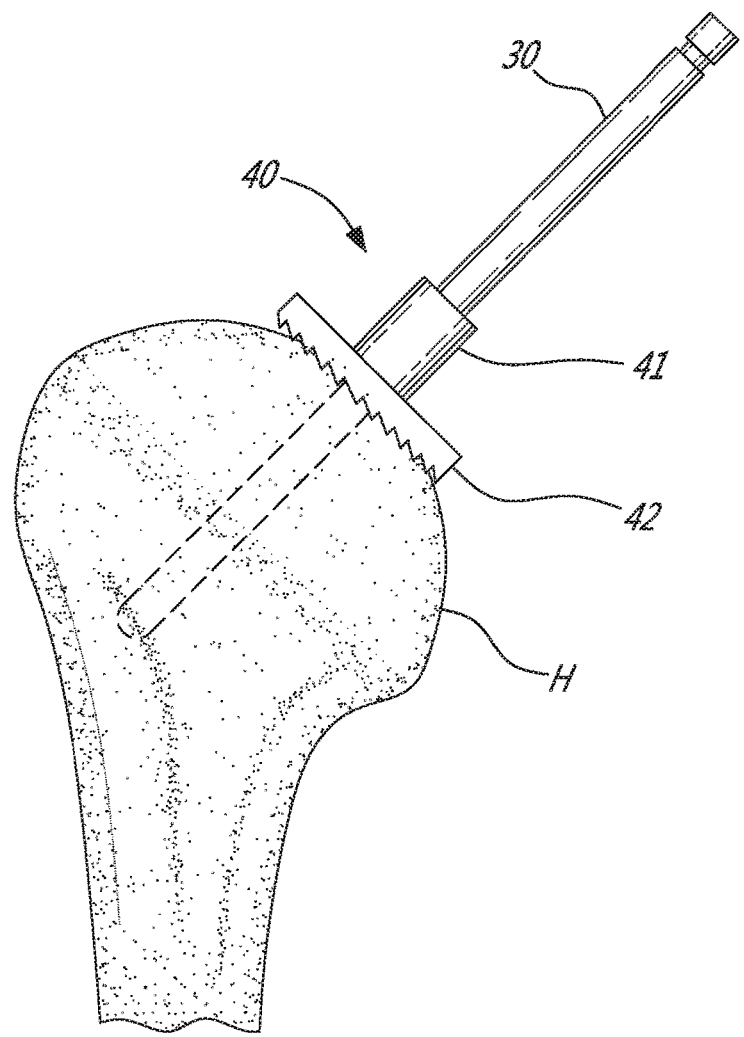
FIG. 8 is a schematic view of the humerus of FIG. 7, with a reamer on the guide rod.
Figure 9:
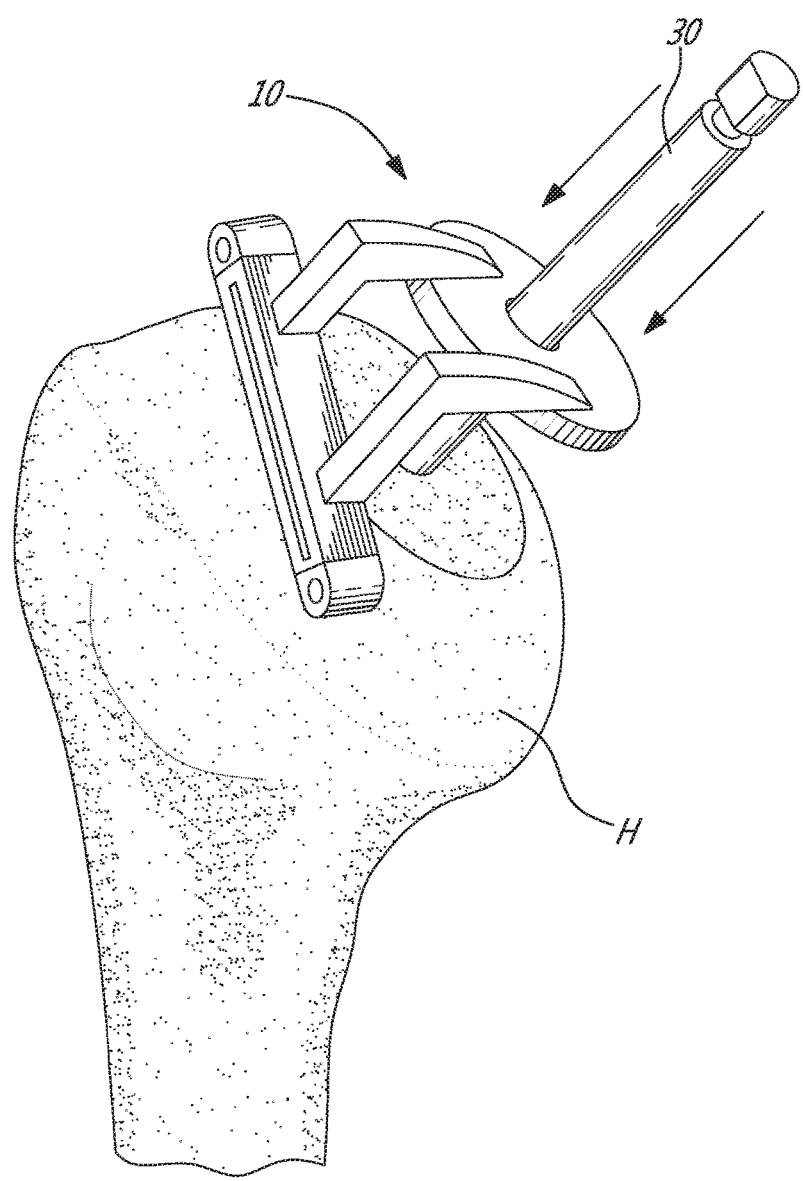
FIG. 9 is a perspective view of the humerus of FIG. 8, with the humerus grafting patient-specific instrument of FIG. 1 being slid on the guide rod.

Referring to FIG. 8, the guide rod 30 is used with a flat reamer 40. The flat reamer 40 is of the type having a hollow cylinder 41 at the end of which is a disc 42. Accordingly, by use of the reamer 40, the humerus H may have its head flattened as shown in FIG. 9. The flattened head could form the implant interface surface of the graft G. It is also considered to use the native surface without machining same, for example if it has a desired shape (e.g., substantially planar), or if the implant interface surface of the implant may be patient specifically shaped for complementary "negative" engagement with the native surface.

Figure 10:
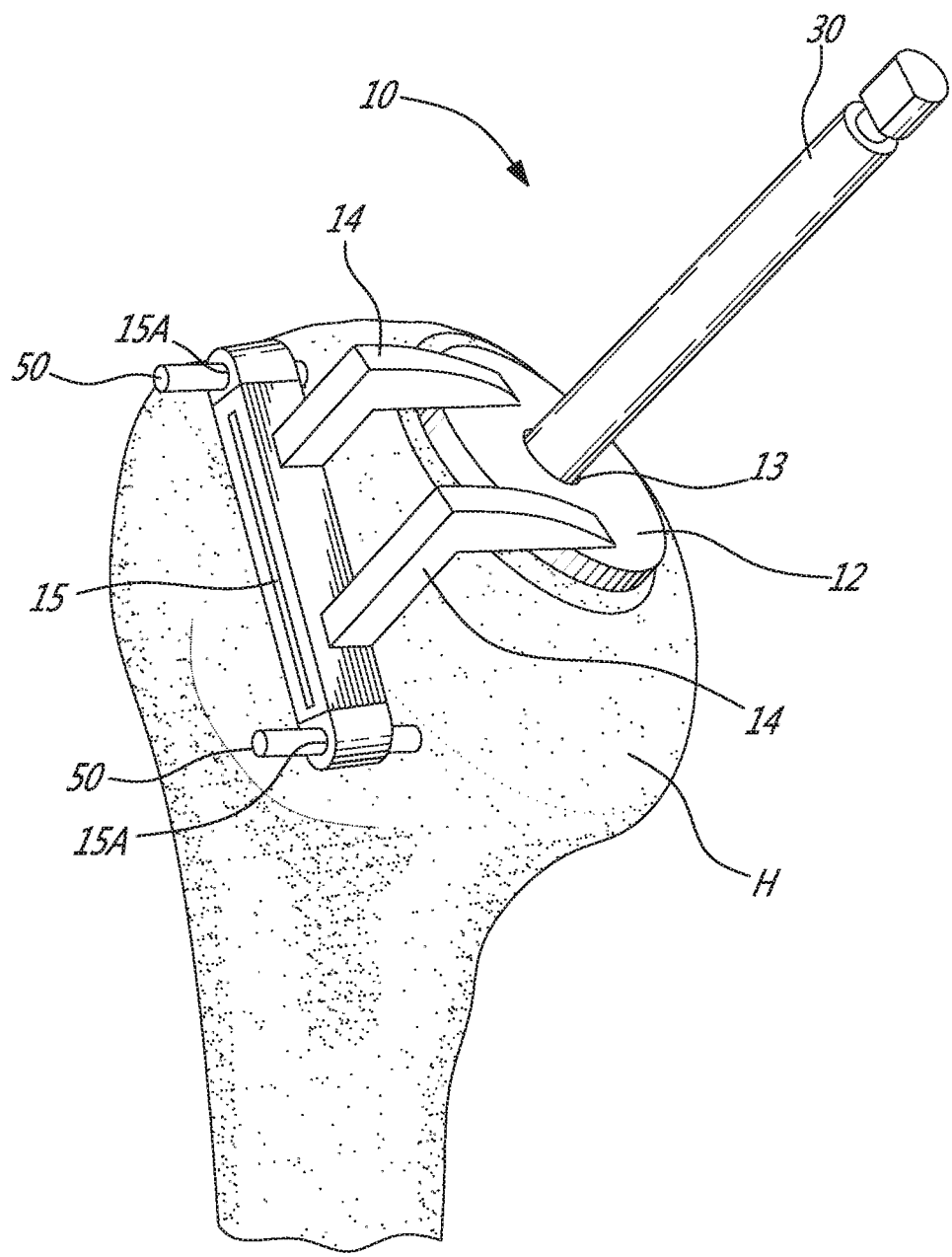
FIG. 10 is a perspective view of the humerus of FIG. 9, with the humerus grafting patient-specific instrument being pinned to the humerus.

Once the head is flattened as in FIG. 9, the humerus grafting patient-specific instrument 10 may be slid onto the humerus H, using the guide rod 30 to form a joint with the base plate 12 of the instrument 10. The diameter of the guide bore 13 of the base plate 12 of the instrument 10 is sized so as to precisely fit onto the guide rod 30. Once the base plate 12 lays flat against the flattened surface of the humerus H (constituting the abutment), as shown in FIG. 10, the cut slot 15 may be pinned to the humerus H by way of pin(s) 50. It is pointed out that, in the illustrated embodiment, the orientation of the instrument 10 relative to the humerus H is of lesser importance than the requirement for the base plate 12 to be flat and in abutment against the humerus H.

Figure 11:
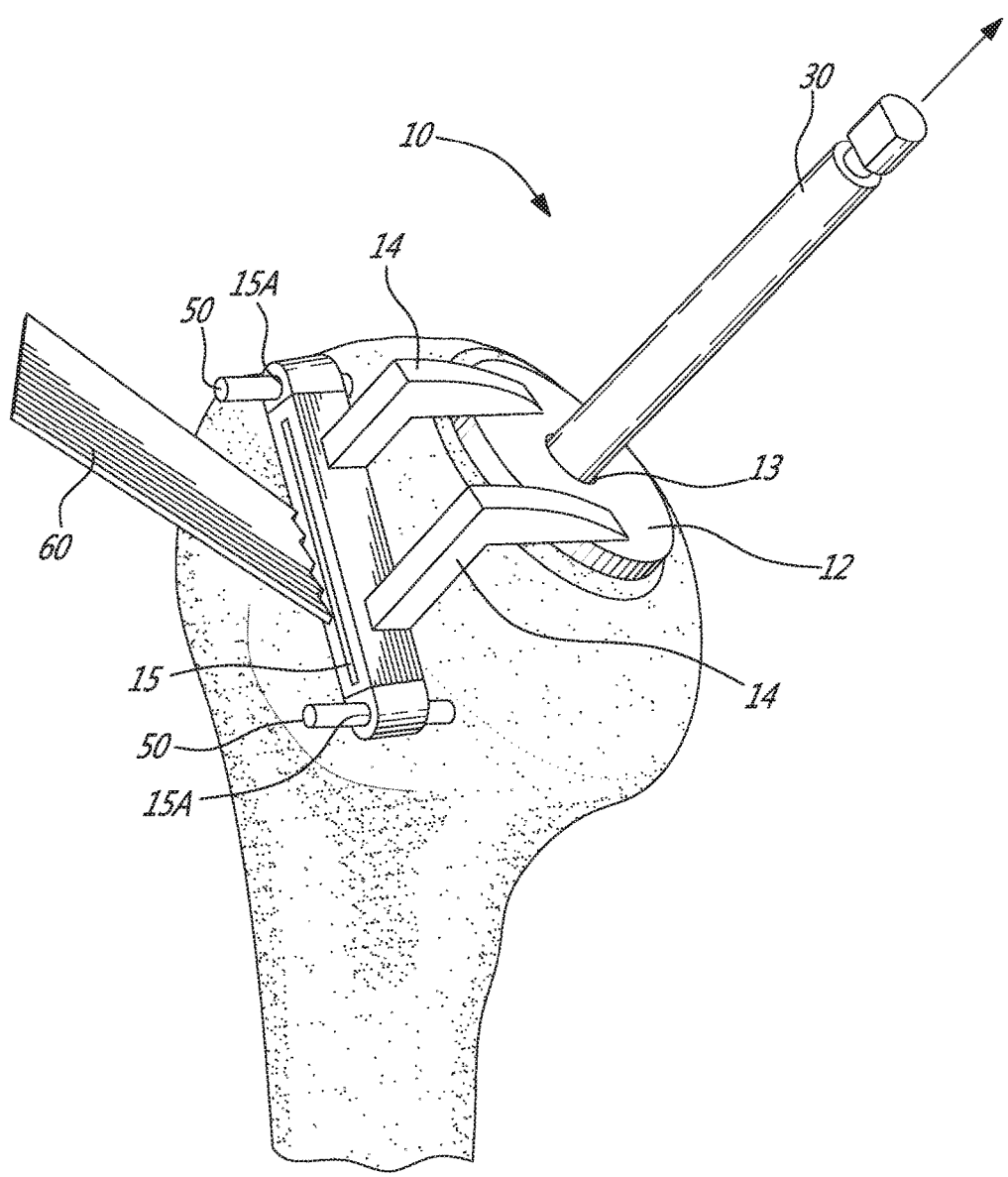
FIG. 11 is a perspective view of the humerus of FIG. 10, with a cut blade guided by the humerus grafting patient-specific instrument of FIG. 1.

Referring to FIG. 11, with the instrument 10 pinned to the humerus H by the pins 50, cut blade 60 may be used in the cut slot 15 to perform a depth cut D, to define the glenoid interface surface of the graft G. It may be required to remove the guide rod 30 prior to performing the depth cut with the cut blade 60 so as not to have the guide rod 30 interfere with the cut blade 60. This is dependent on the depth of the guide rod 30. In such a case, the pins 50 ensure that the instrument 10 remains anchored to the humerus H during the depth cut.

Figure 12:
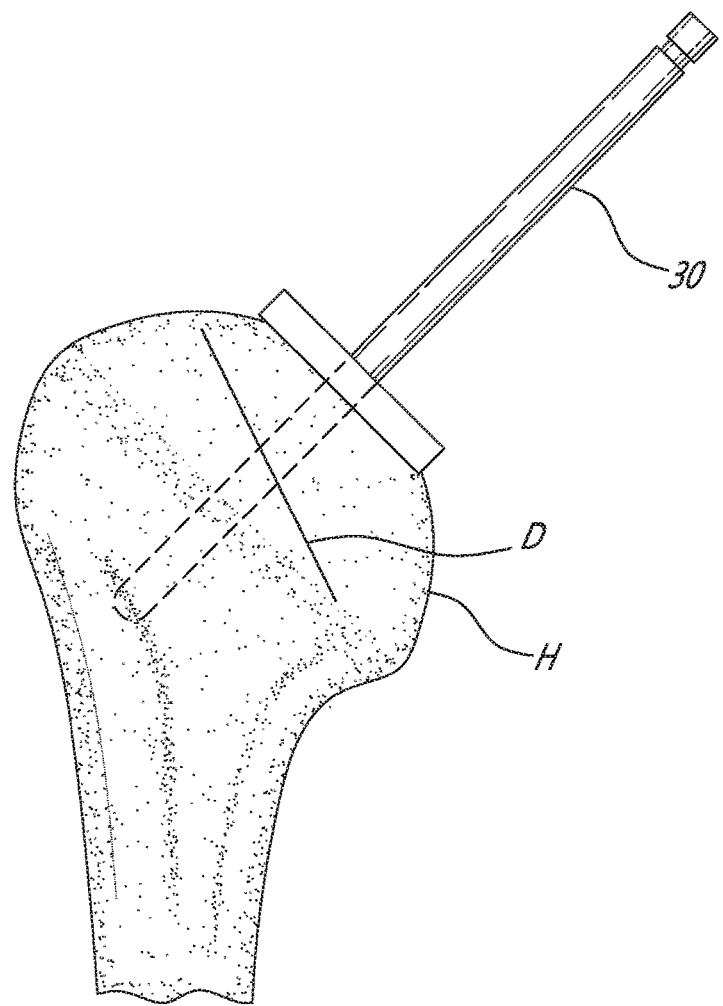
FIG. 12 is a schematic side view of the humerus of FIG. 7, with a depth cut.
Figure 13:
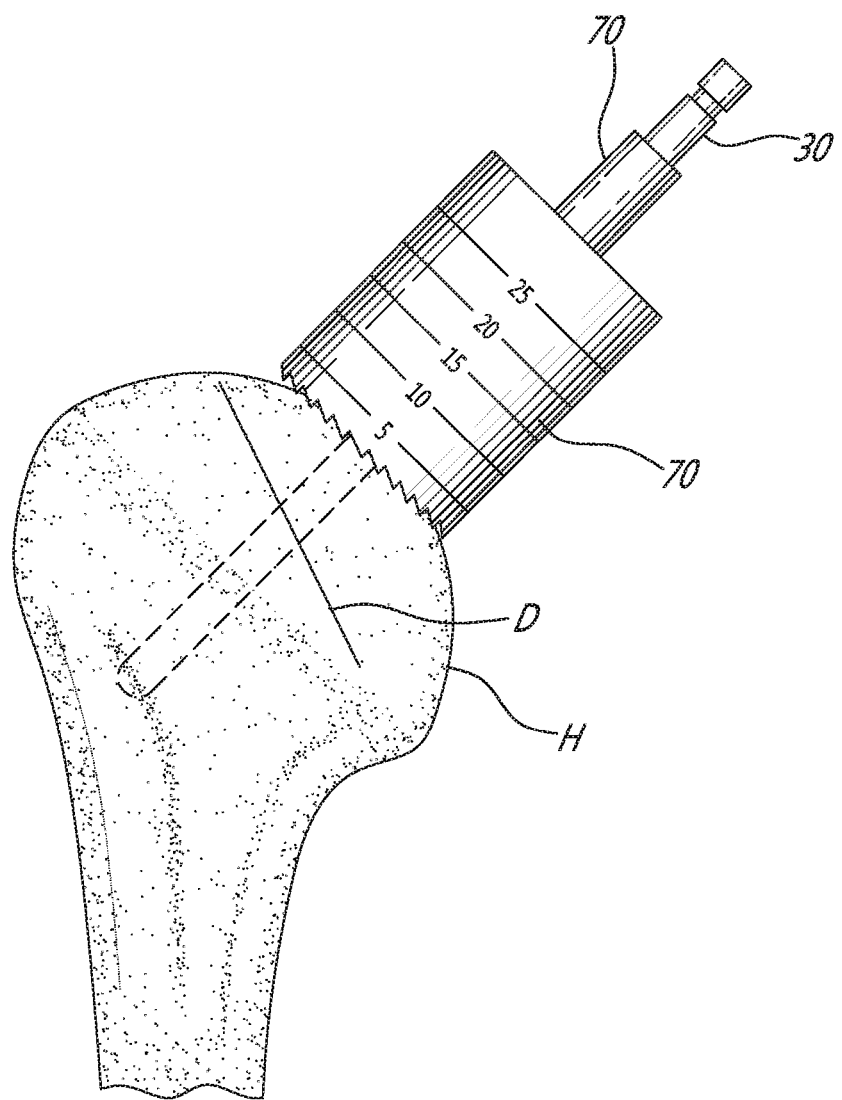
FIG. 13 is a schematic view of the humerus of FIG. 12, with a bell saw on the guide rod.
Figure 14:
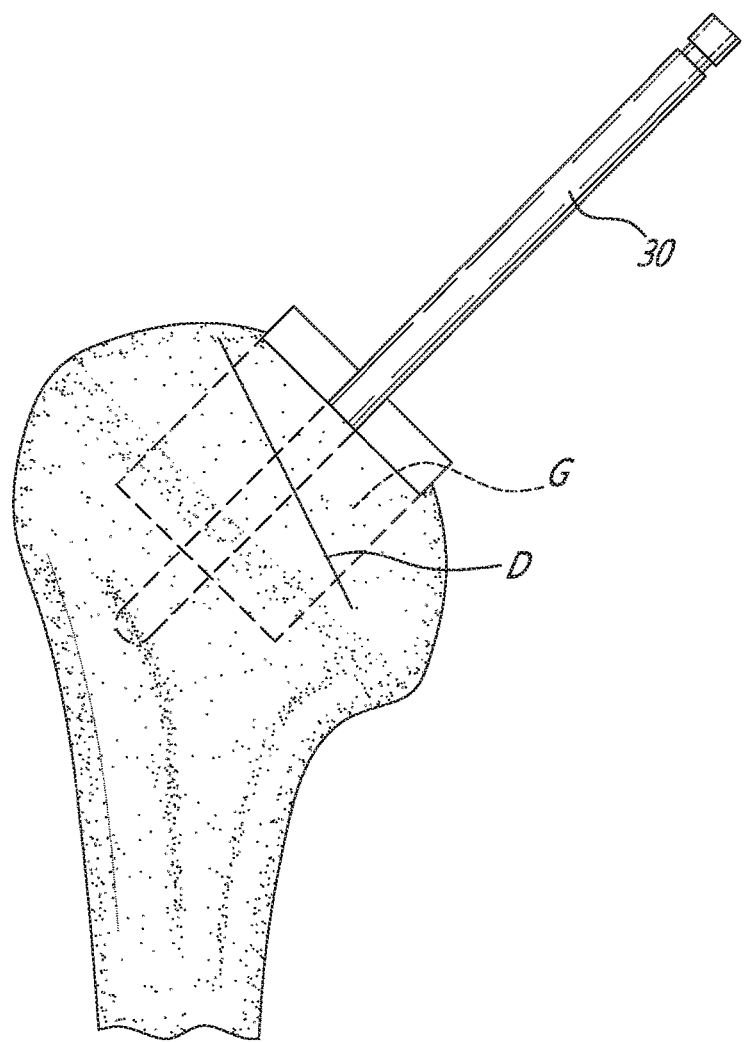
FIG. 14 is a schematic view of the humerus of FIG. 13, with lateral cuts.

As shown in FIG. 12, once the depth cut D is made, the guide rod 30 may be reinserted into the humerus H, for a bell saw 70, also known as a cylindrical reamer, to be used to perform the lateral cut, as shown in FIG. 14. This results in the detachment of the humerus graft G from a remainder of the humerus H. The bell saw 70 may have a depth scale thereon, to provide a visual display of depth.

Figure 15:
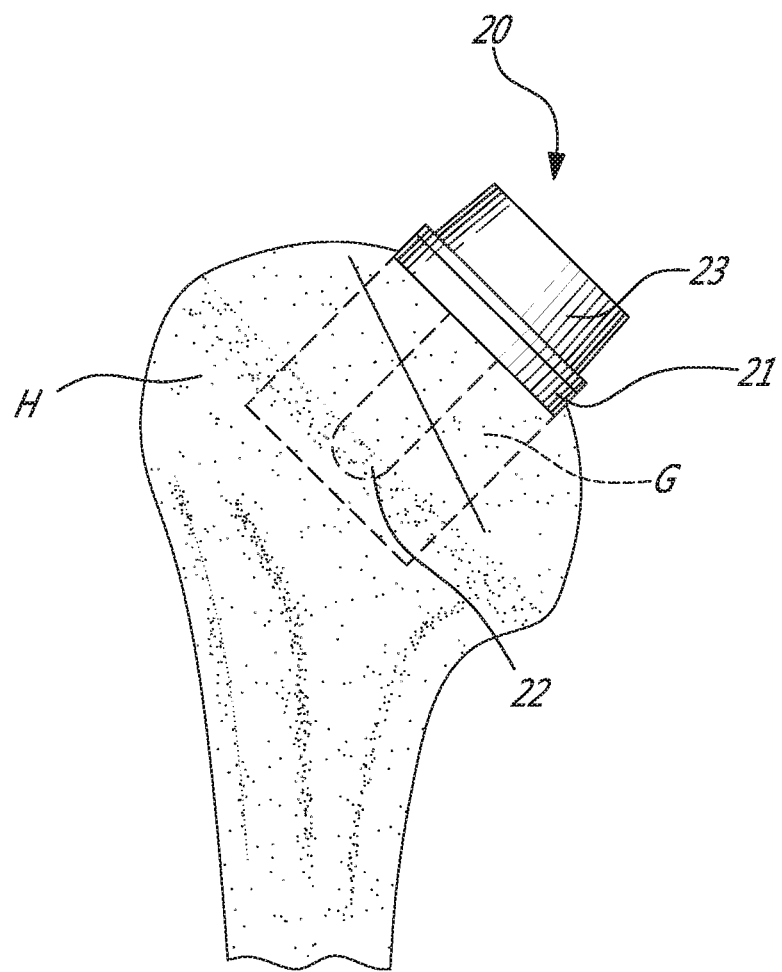
FIG. 15 is a schematic view of the humerus of FIG. 14, with the glenoid implant inserted into a graft for removal.
Figure 16:
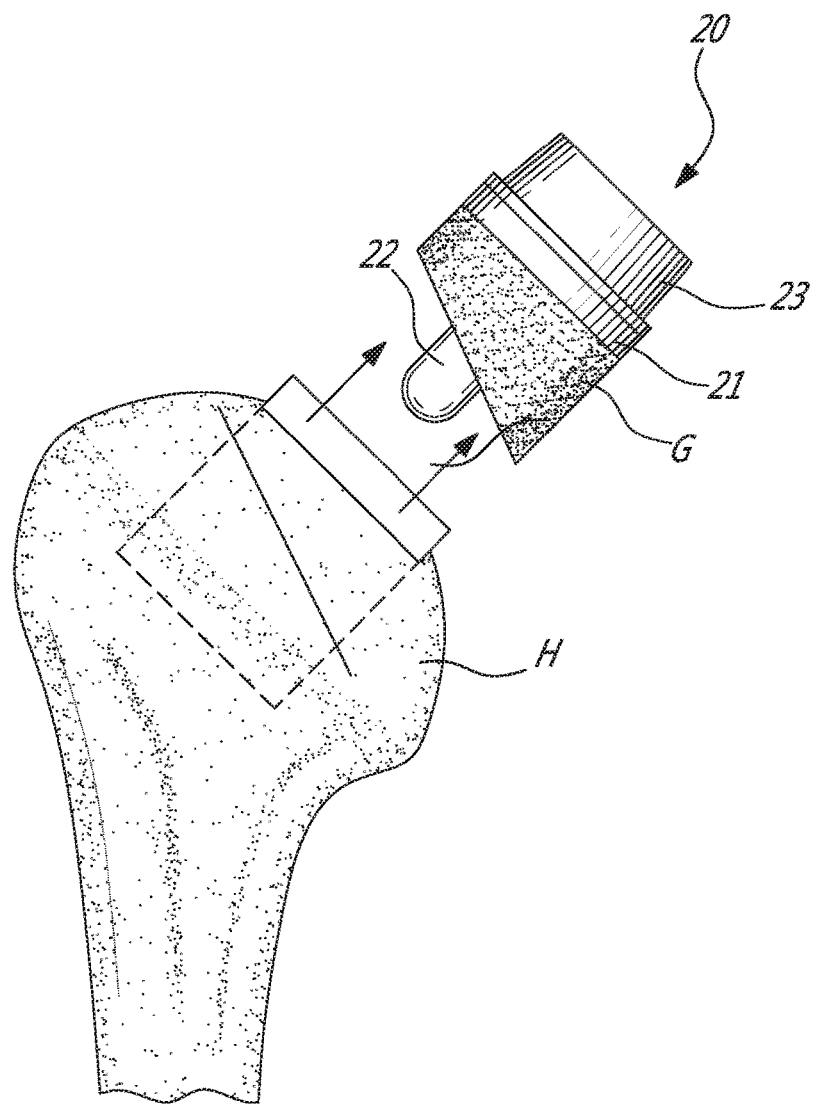
FIG. 16 is a schematic view of the humerus of FIG. 16 with the humerus graft being harvested with the glenoid implant.

In FIG. 15, there is illustrated a technique for removing the humerus graft G, using the glenoid implant 20. By this method, the glenoid implant 20 is forced into the humerus graft G, requiring for example the machining of a bore of adequate dimension in the humerus graft G, until the base plate 21 of the glenoid implant 20 is flush against the surface of the humerus graft G. The humerus graft G is harvested as shown in FIG. 16 by pulling out the glenoid implant 20. At that point, it is possible to install the assembly of humerus graft G and glenoid implant 20 in the manner shown in FIGS. 4 and 6, and this may require some reaming and peg drilling to the glenoid cavity C. Fasteners of any appropriate type, and tools (e.g., impactor) may be used to properly implant the combination of the humerus graft G and glenoid implant 20. Also, cement or like adhesive can be used to fasten the graft to the implant.

The embodiment described above for the instrument 10 is commonly used when glenoid deformities are generally planar, or machined to be planar as planned. This is a common occurrence and is advantageous as flat reaming minimizes subchondral bone sacrifice. The geometry of the graft G may be defined as having a cylindrical body. A peg bore may be defined along the central axis of the cylindrical body, for the implant peg to pass through the cylindrical body. The central axis of the cylindrical body may be normal to the first end surface of the cylindrical body, whereas the second end surface of the cylindrical body is oblique. In other words, a plane in which lies the second end surface is not parallel to a plane in which lies the first end surface. The angle between the planes is less than 90 degrees, and is commonly between 5 and 45 degrees, although it could be out of that range. Therefore, all three surfaces of the graft G may be machined, in three different steps, while being on the native bone. The machining of the peg bore may be in a fourth separate step, or may consist in the removal of the guide pin 30, the guide pin 30 being selected to have a diameter matching that of the peg 22. Although described as being donated by the humerus, the graft G may be harvested from other sites, such as the iliac crest.

Now that the humerus grafting patient specific instrument 10 has been described as used for a flat glenoid surface, another embodiment of a humerus grafting patient specific instrument is set forth, for a frusto-spherical glenoid cavity, i.e., the glenoid cavity is a sphere segment surface. Indeed, in some instances, the erosion is spherical with a glenoid surface medialization due to wear. This is for instance shown in FIG. 18.

Figure 17:
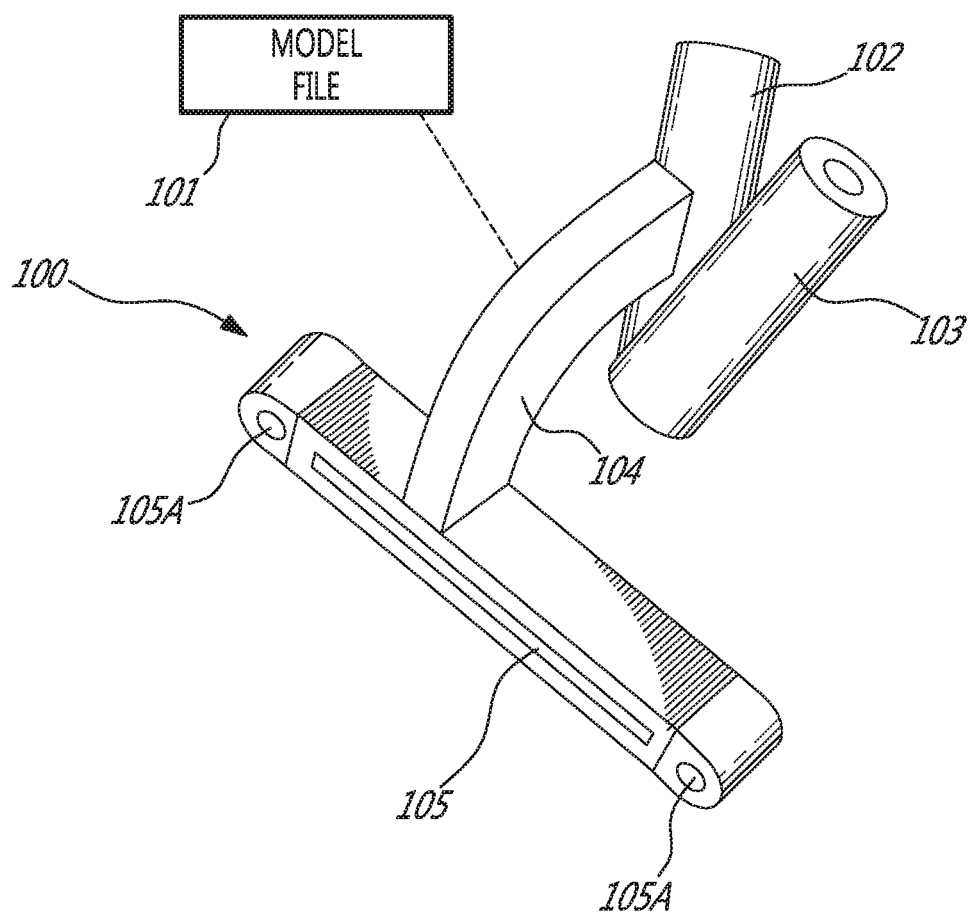
FIG. 17 is a perspective view of a humerus grafting patient specific instrument in accordance with a second embodiment.

Therefore, referring to FIG. 17, there is illustrated a humerus grafting patient specific instrument 100 to be used for hemispherical or frusto-spherical glenoid cavities. In similar fashion to the instrument 10, the instrument 100 is patient specific and has a model file 101 featuring modelisation of the patient's anatomy obtained pre-operatively. The instrument 100 has a first guide 102 and a second guide 103, both generally elongated cylindrical portions with channels of circular section that would be mounted onto pins and thus form sliding joints. A depth leg 104 projects from the first guide 102 and has a cut slot 105 (with pin guides 105A) at an end thereof.

Figure 18:
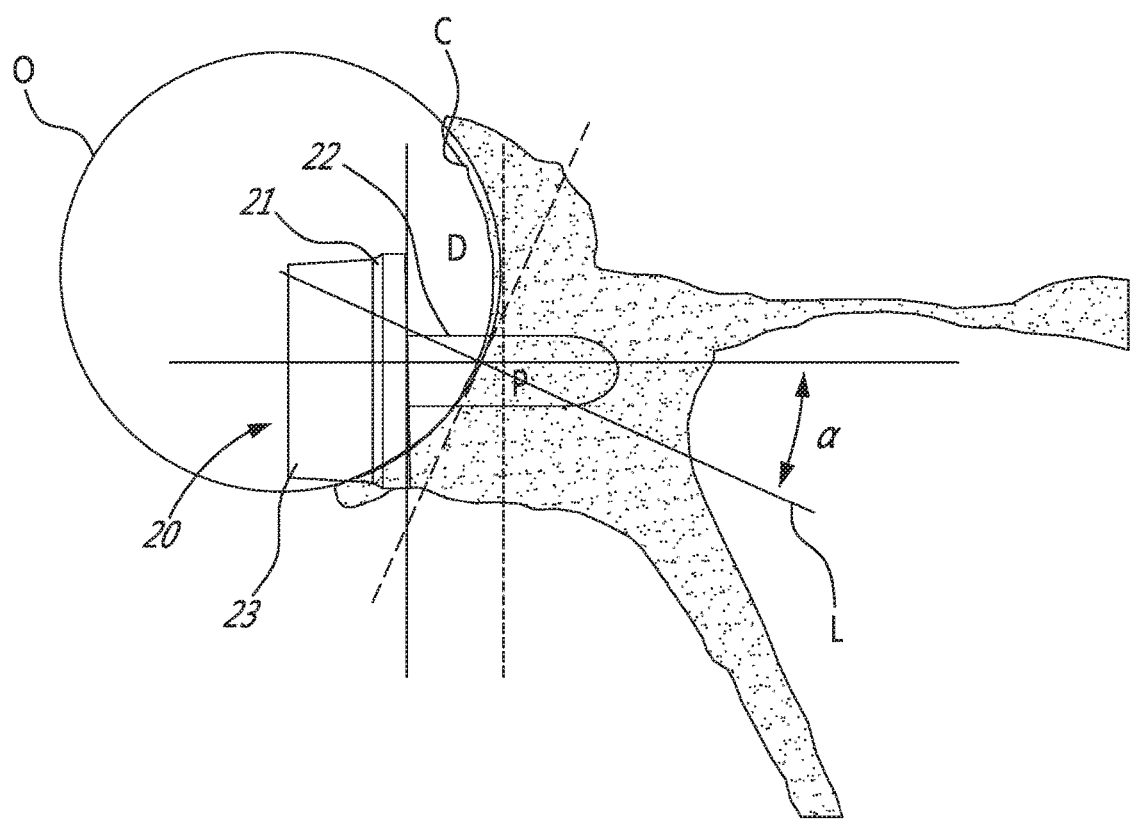
FIG. 18 is a side view of a glenoid implant relative to a glenoid cavity in accordance with the second embodiment.

Referring to FIG. 18, a schematic planning view is provided showing the desired positioning of the glenoid implant 20 relative to the glenoid cavity C. As observed, the glenoid cavity C has a circular outline (circle O shown in FIG. 18), indicative of a frusto-spherical cavity, with a distance D between an underface of the baseplate 21 of the glenoid implant 20 and a bottom of the glenoid cavity C. The depth D is representative of the height of the humerus graft G to be harvested from the humerus H. Moreover, angle α is also to be taken into consideration, as the angle between the axis of the peg 22 of baseplate 21 and line L. Line L passes through point P at the intersection of the axis of the peg 22 with the circle O, and through the center of the circle. All these parameters are obtained preoperatively from the surgeon planning of the implanting procedure relative to the glenoid surface and are part of the model file 101. These parameters are descriptive of the spatial geometry of the graft G to interface the implant 20 to the reamed glenoid cavity C.

Figure 19:
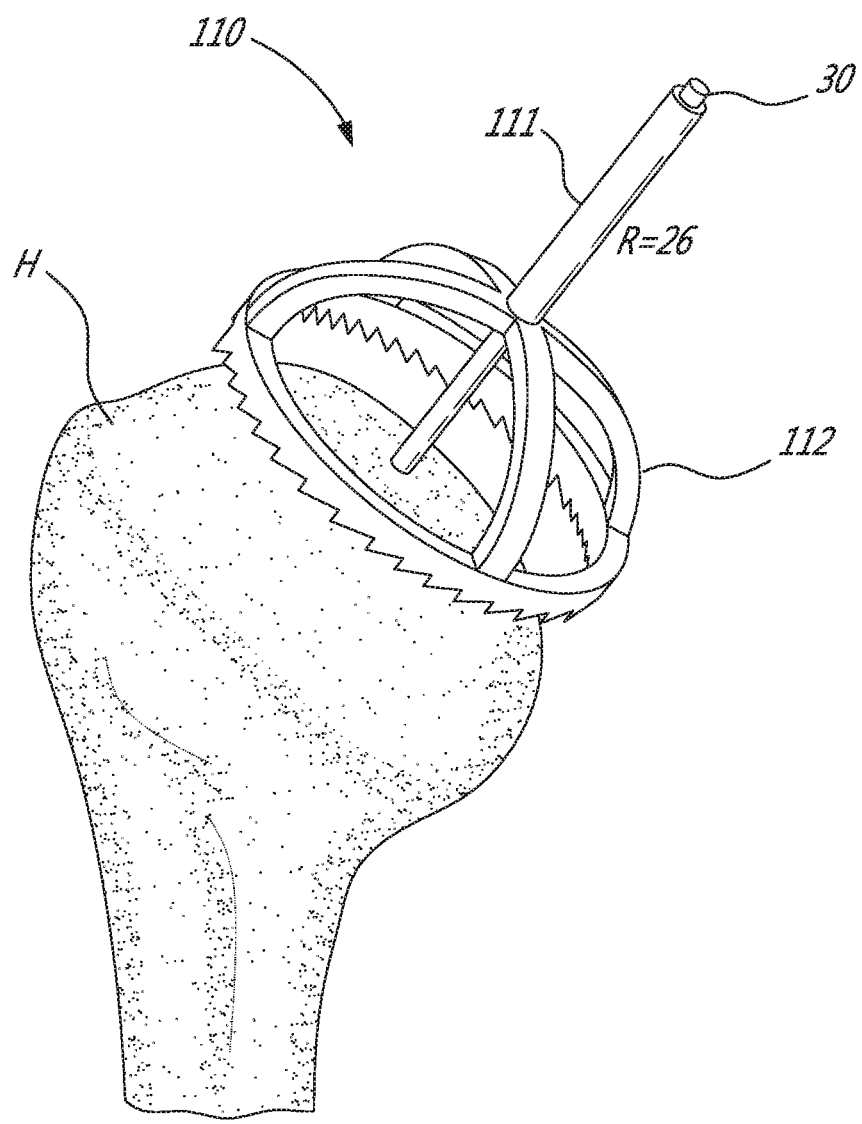
FIG. 19 is a perspective view of the humerus with a hemispherical reamer.
Figure 20:
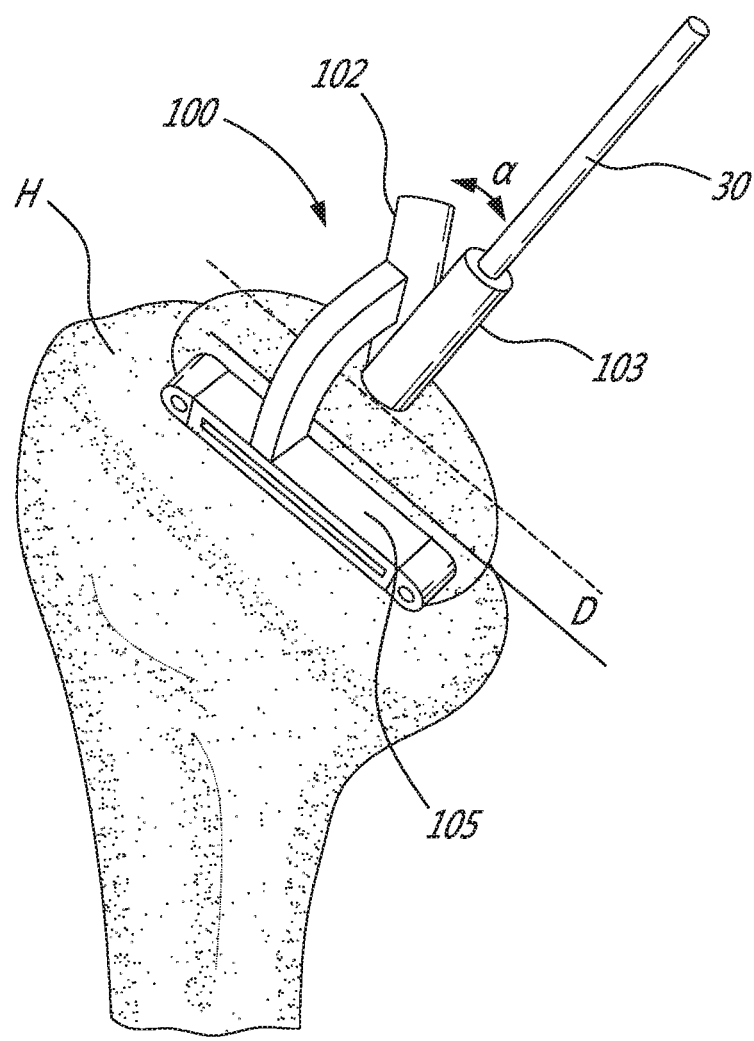
FIG. 20 is a perspective view of the humerus of FIG. 19, with the humerus grafting patient-specific instrument of FIG. 17.

Referring to FIG. 19, in order to start the grafting procedure, a hemispherical reamer 110 is used to surface the humerus head H into a frusto-spherical shape. Hemispherical reamer 110 has a hollow cylinder 111 that is cannulated to be mounted on the guide rod 30. A saw edge 112 is sized as a function of the dimension of the diameter of the circle O of FIG. 18. Accordingly, various sizes of the hemispherical reamer 110 may be provided, with the operator selecting the appropriate size based on the pre-operative planning and on the model file 101. Hence, the reamed humerus head H has the glenoid interface surface machined onto it.

Once the humerus head has been shaped, the instrument 100 may be positioned thereon using the guide rod 30. The guide rod 30 serves as a shaft for the second guide 103, with the angle between the first guide 102 and the second guide 103 being angle α.

Figure 21:
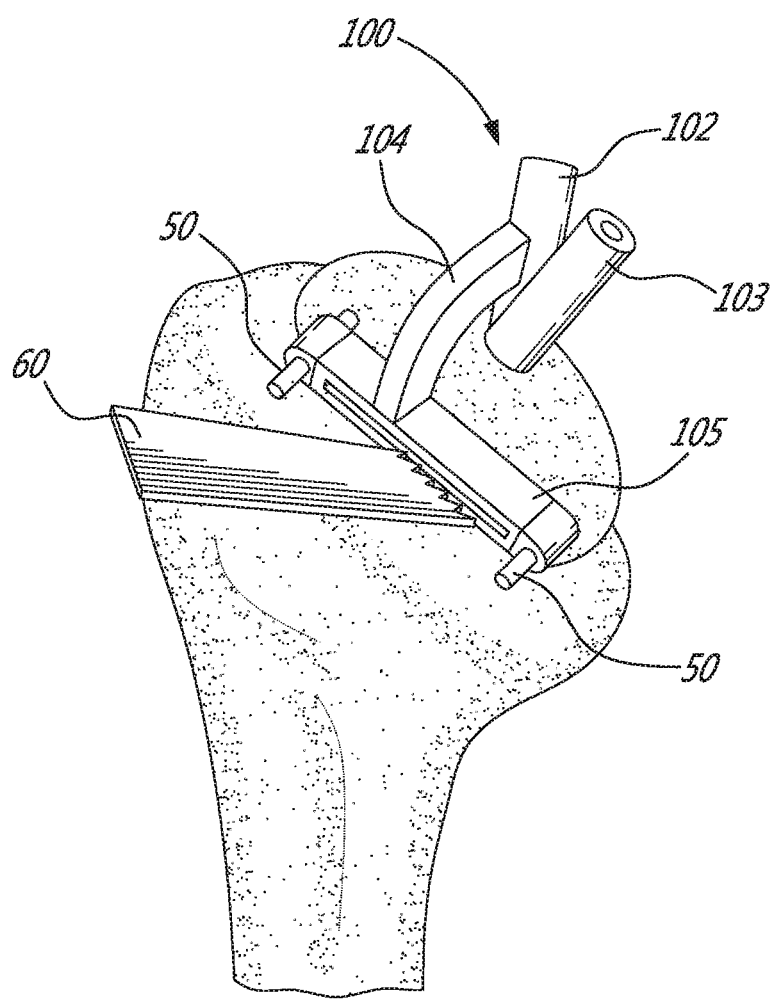
FIG. 21 is a perspective view of the humerus of FIG. 20, with a cut blade used with the humerus grafting patient-specific instrument of FIG. 17.
Figure 22:
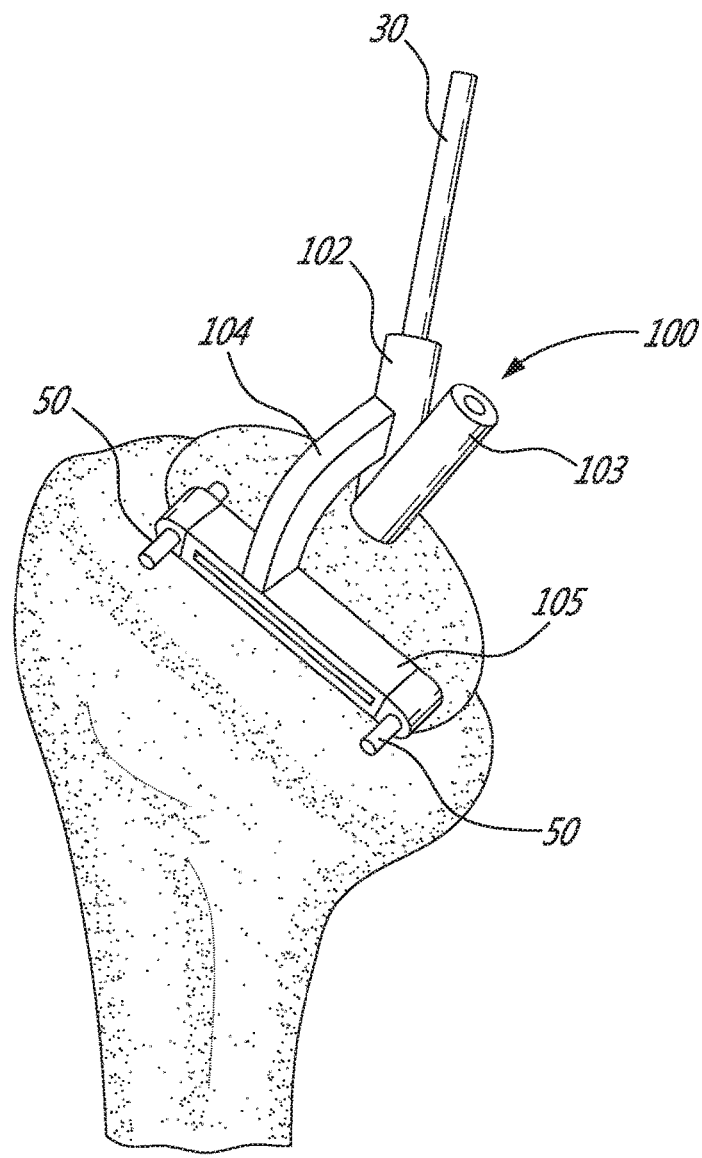
FIG. 22 is a perspective view of the humerus of FIG. 21, with a guide pin being repositioned.

Referring to FIG. 21, once the instrument 100 abuts against the humerus H, it may be pinned using pin(s) 50. The guide rod 30 may be removed for the cut blade 60 to perform a depth cut of depth D, to form the implant interface surface of the graft G. Once the depth cut has been made, the guide 130 may be repositioned onto the humerus H, but this time using the first guide 102, as shown in FIG. 22.

Figure 23:
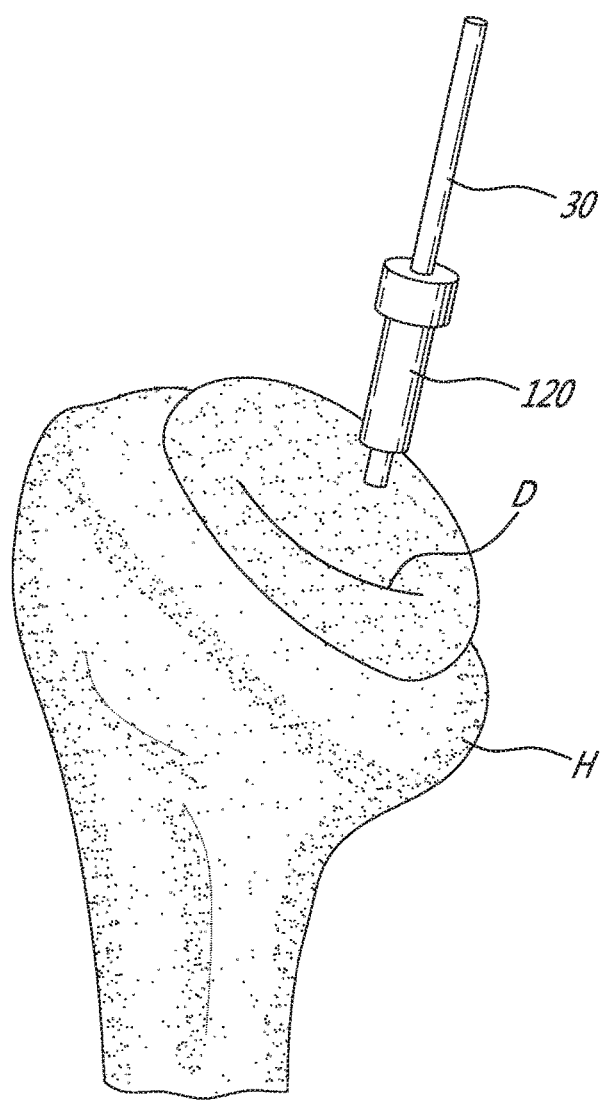
FIG. 23 is a perspective view of the humerus of FIG. 22, with a depth cut thereon.

Referring to FIG. 23, a drill tool 120 may then be used to machine a bore in the humerus H, which bore is sized based on the diameter of the peg 22 of the implant 20, as it will receive the peg 22 therein.

Figure 24:
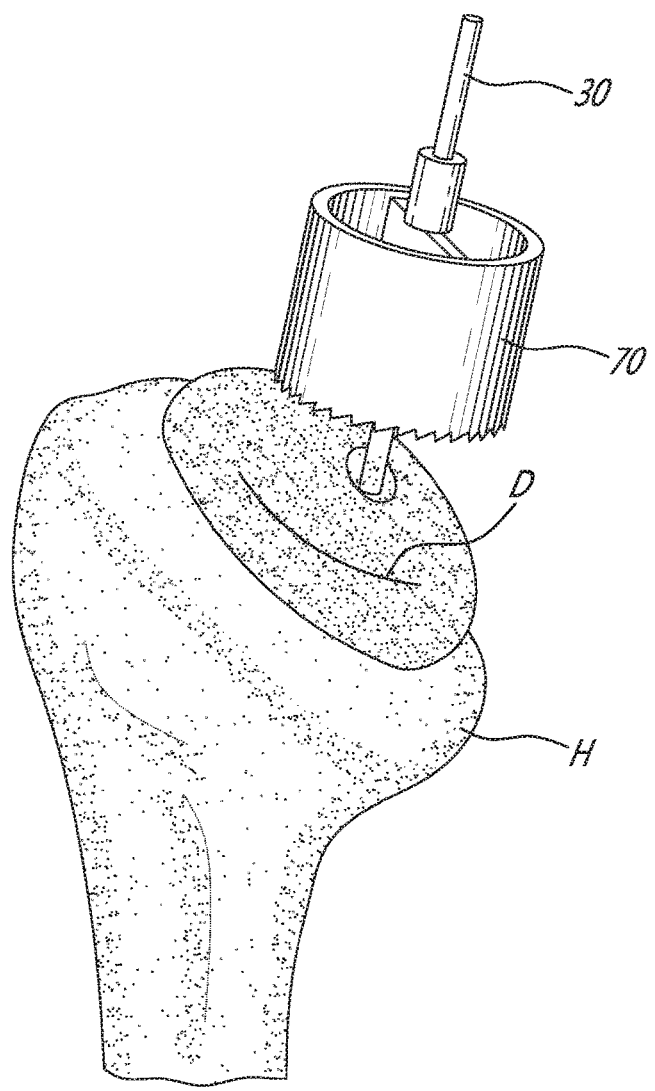
FIG. 24 is a perspective view of the humerus of FIG. 23, with a saw bell.

Referring to FIG. 24, the saw bell 70 may then be used in order to define the size of the graft G to be harvested. Accordingly, based on the preceding steps, humerus graft G is shaped for use in the configuration of FIG. 18, and may be harvested.

Figure 25:
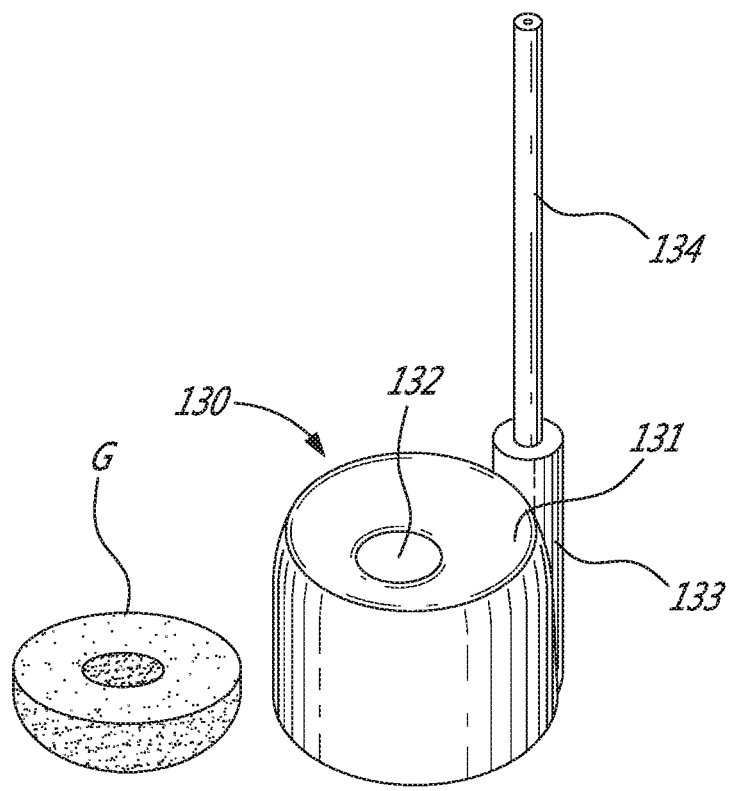
FIG. 25 is a perspective view of a patient-specific barrel with a harvested humerus graft.

In order to implant it properly (or implant the graft G harvested using the instrument 10) and replicate the planning by setting the graft axial rotation appropriately, different tools may be devised, such as barrel 130 of FIG. 25. The barrel 130 has a cavity 131 that is shaped in patient specific manner, in similar fashion to the instruments 10 and 100. As such, barrel 130 may have a model file. A peg bore 132 is a bottom of the cavity 131, and sized and positioned specifically based on the planned interrelation between the peg 22 and the graft G. Accordingly, the alignments of the peg bore 132, the barrel 130 and the peg bore in the humerus graft G ensure that a single orientation of the humerus graft G in the barrel 130 is achieved, for insertion of the peg 22 in the manner shown in FIG. 26. The barrel 130 further comprises a guide 133 that cooperates with a pin 134 to form a sliding joint.

Figure 26:
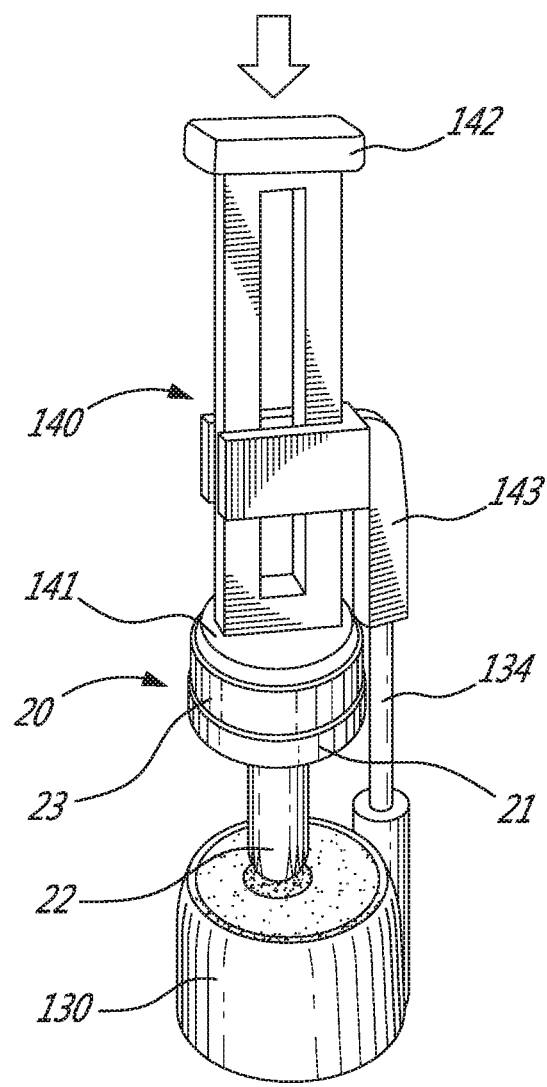
FIG. 26 is a perspective view of the patient-specific barrel with impactor, glenoid implant and graft.
Figure 27:
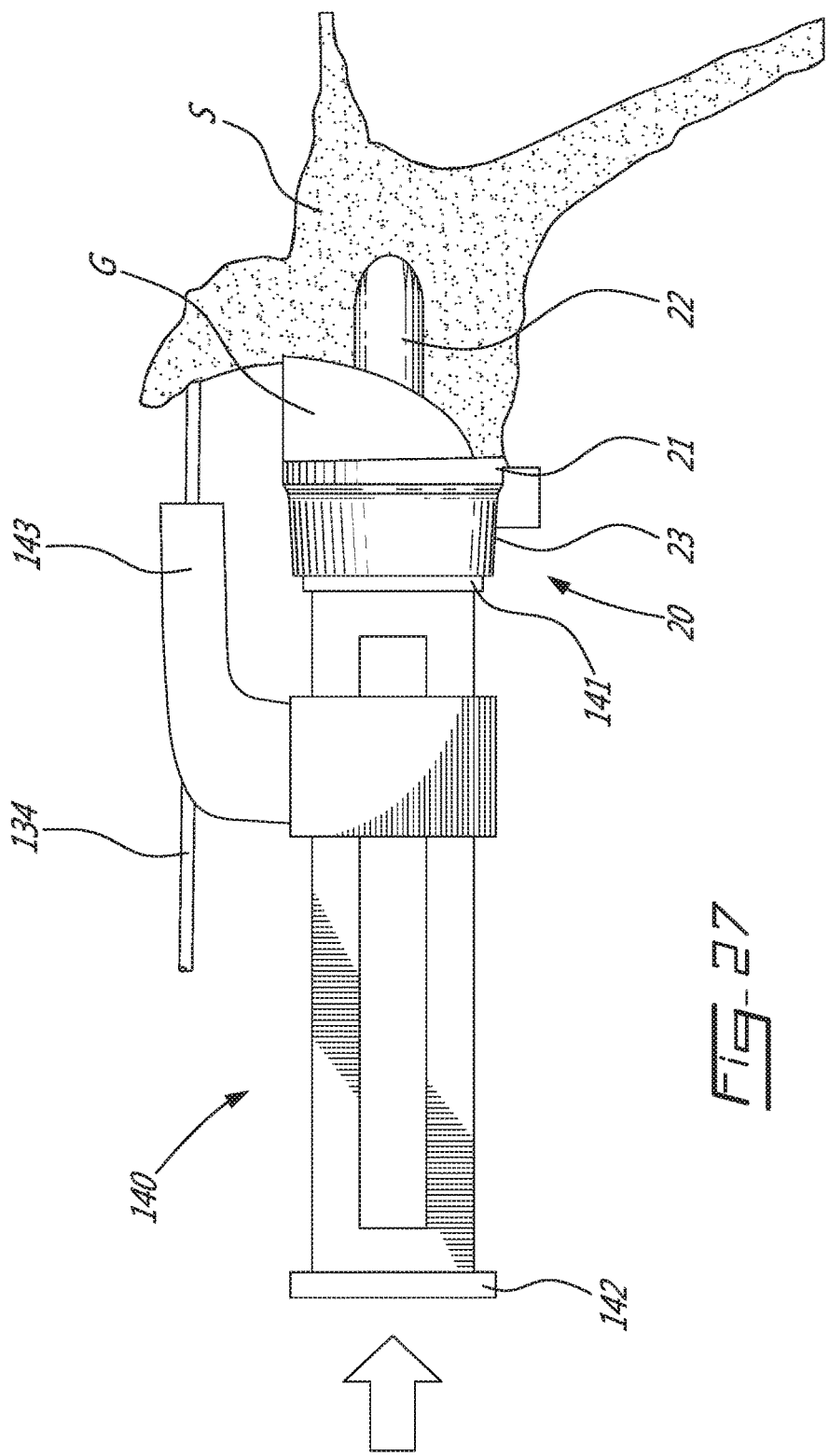
FIG. 27 is a side view of an impactor relative to the glenoid cavity in the process of implanting the glenoid implant and graft.

As shown in FIG. 26, an impactor 140 has an implant end 141 devised to support the tapered head 23 of the implant 20. The impactor 140 also has at an opposite end an impact end 142 adapted to be impacted for implanting the implant 20. The impactor 140 also has a guide 143 that will collaborate with the pin 134. This is shown particularly in FIG. 27 in which it is observed that the impactor 140 is guided by the implanted pin 134 to perform the impacting action. The graft could be cemented to the baseplate and not impacted.

Figure 28:
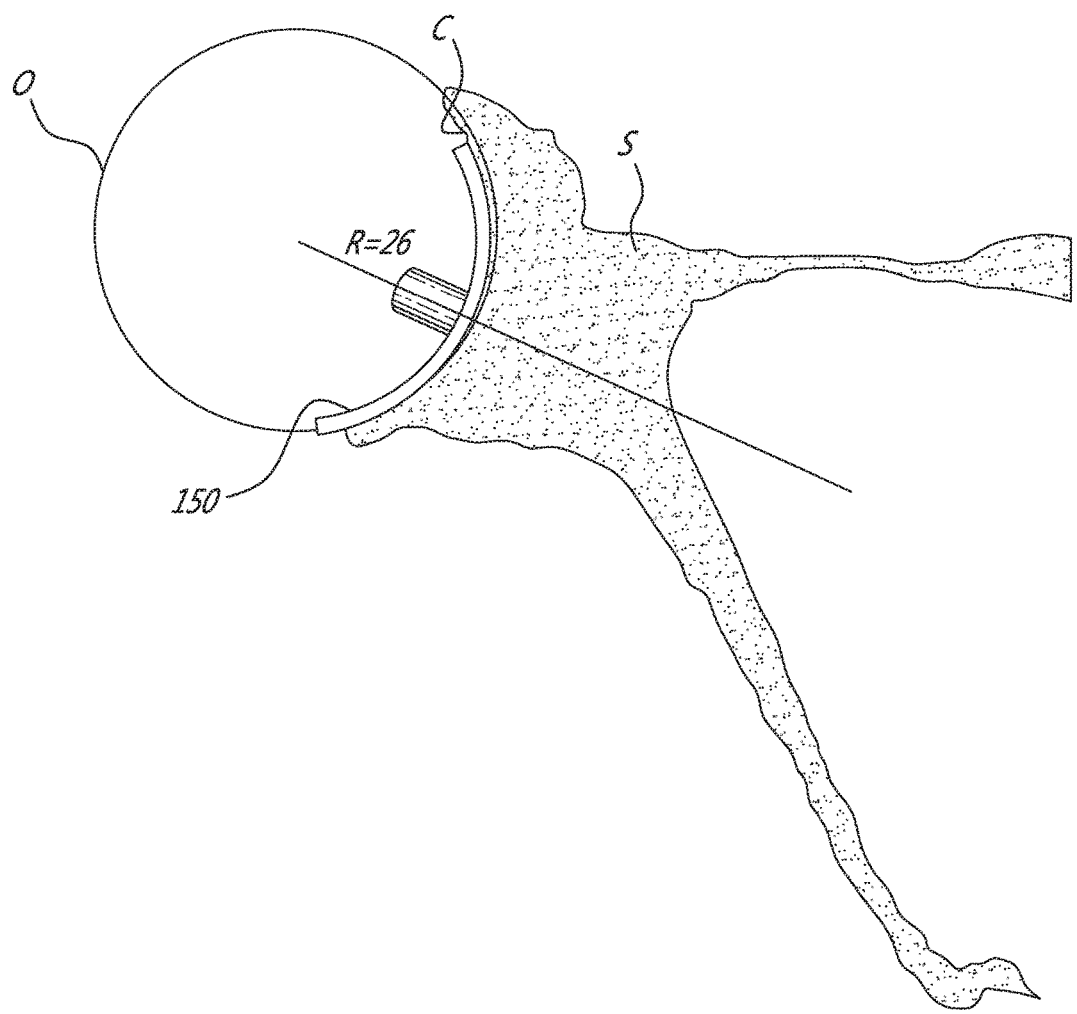
FIG. 28 is a side view of a reamer reaming the glenoid cavity for receiving the humerus graft harvested in FIGS. 17 to 24.
Figure 29:
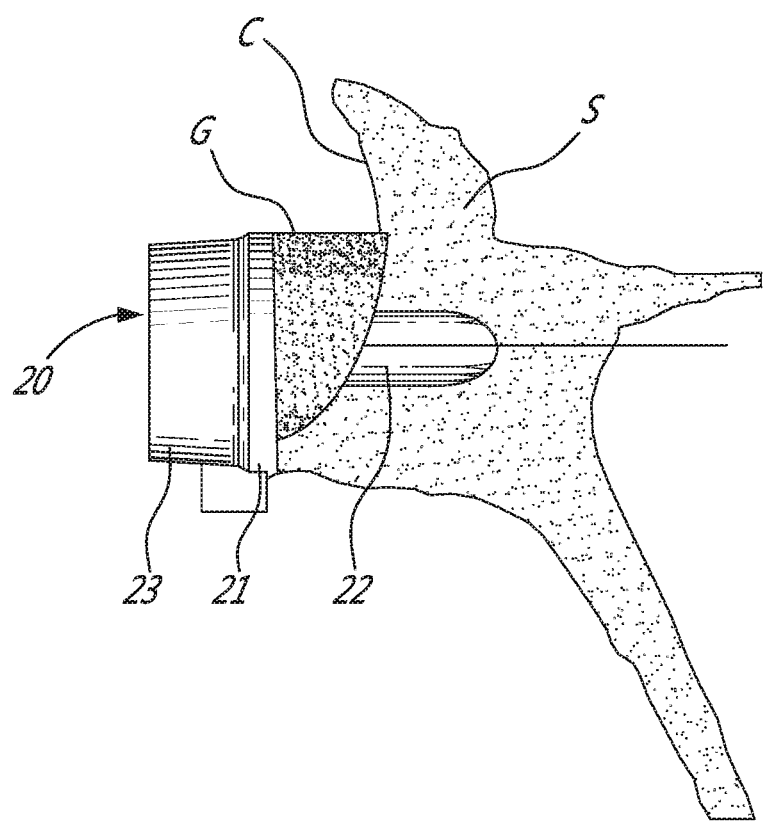
FIG. 29 is a side view of the humerus graft, glenoid implant in the resurfaced glenoid cavity.

Referring to FIG. 28, it may however be necessary to machine the glenoid cavities C using a reamer 150 having an arcuate cutting tool 151. It is pointed out that the barrel 130 may be used to machine the glenoid cavities so as to define the peg bore into the glenoid. Accordingly, the implant 20 and the harvested graft G may be implanted in the reamed glenoid cavity C in the manner shown in FIG. 29.

The geometry of the graft G may be defined as having a cylindrical body, although an axial length of the cylindrical body may be close to zero at a location. A peg bore may be defined along the central axis of the cylindrical body, for the implant peg to pass through the cylindrical body. The central axis of the cylindrical body may be normal to the first end surface of the cylindrical body, whereas the second end surface of the cylindrical body is spherical. The center of the spherical surface is not aligned with the central axis of the cylindrical body, i.e., it is not coincident with the central axis. Therefore, all three surfaces of the graft G may be machined, in three different steps, while being on the native bone. The machining of the peg bore may be in a fourth separate step. The machining of the peg bore may be in a fourth separate step, or may consist in the removal of the guide pin 134, the guide pin 134 being selected to have a diameter matching that of the peg 22. Although described as being donated by the humerus, the graft G may be harvested from other sites, such as the iliac crest.

Therefore, the method can generally be described as a method for creating a graft. According to the method, a cut guide instrument 10 or 100 is obtained, and is specific to a patient's anatomy. The instrument 10 or 100 is the result of pre-operative planning in which the patient's anatomy is modeled, and the spatial geometry of a graft is defined from the surgeon planning by the planning software. Intraoperatively, an exposed surface of a donor bone is resurfaced, to form an implant interface surface (in the case of instrument 10) or a bone interface surface (in the case of instrument 100) of the graft G. The cut guide instrument 10 or 100 is then secured to the donor bone. Using the cut guide instrument 10 or 100, a depth cut in performed the donor bone to form the other of the implant interface surface or the bone interface surface of the graft G. It may be required to further machine the graft G, or the graft G may be harvested right away, for example if the resurfacing has also been used to define the lateral surfaces of the graft G.

While the method described above provides an example of shoulder surface, the method could also be used with other joints, or for a non-reverse shoulder surgery.

Figure 30:
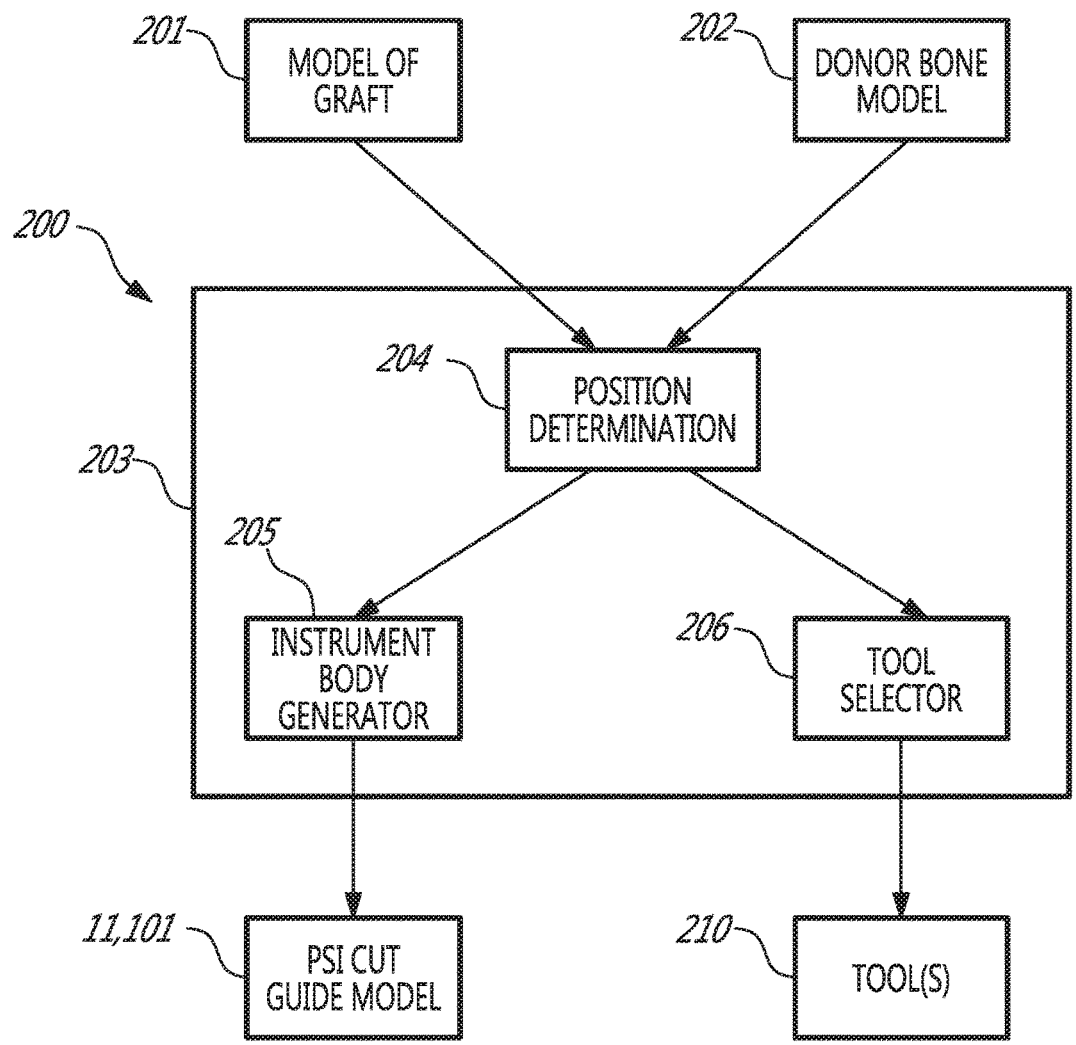
FIG. 30 is a block diagram of a system for generating a model of a patient specific cut guide instrument for harvesting a graft, in accordance with the present disclosure.

Referring to FIG. 30, there is illustrated a system 200 for generating a model of a patient specific cut guide instrument, such as 10, 100, for harvesting a graft, such as G, for subsequent fabrication and used based on the methods illustrated in FIGS. 1-29. In order to generate the model of the patient specific cut guide instrument, such for example at 11, 101 in FIGS. 1, 17 and 30, the system 200 must have a model 201 of the graft G. The model 201 is for example the result of pre-operative planning, in which a virtual positioning and orienting of an implant is done on images of a bone. This may be illustrated for example by FIGS. 3, 4 and 18, with the graft G being defined by an implant interface surface, a bone interface surface, and a spatial geometry therebetween. The model is specific to a patient, in that it results from an analysis of the patient's data (imagery of bone, for example in 3D, patient condition, etc). The system 200 may also have a model 202 of the donor bone, such as the humerus H. The graft G will be harvested in the donor bone, and therefore the system 200 determines how to alter the donor bone to harvest the graft G, using the model 202. As described previously, the patient specific cut guide instrument 10 is used for harvesting the graft for subsequent implanting without alterations to the outer surface of the graft G, i.e., after harvesting, the graft G already has a geometry corresponding to the model of the graft 201. Some trivial machining may occur after harvesting, such as machining a peg hole of appropriate dimension in the hole remaining from the pin guide 30. However, such machining is not to alter the outer surface of the graft B, i.e., the cylindrical body and its ends.

A patient-specific instrument generator 203 outputs the model 11, 101 of the patient specific cut guide instrument 10, 100. The patient-specific instrument generator 203 has a processor unit for operating modules that generate data resulting in the model 11, 101, using models 201 and 202. The patient-specific instrument generator 203 may have a position determination module 204 for orienting and positioning a guide axis or axes, taking into consideration the spatial geometry of the graft G, via the model 201, to make sure there is sufficient bone available for the graft G, without damaging what must remain of the donor bone, as per model 202. As observed in FIGS. 1-29, the axes are used to correctly position and orient the instrument 10, 100 on the donor bone, and to guide the tools altering the bone. The position determination module 204 may also position an abutment on the model 202 of a donor bone as a function of the spatial geometry. This may include identifying that the donor bone must be resurfaced to define the abutment, as in FIGS. 8 and 19.

Once the position determination module 204 has produced the orientation and position of the axis, and determined the abutment (including resurfacing), an instrument body generator module 205 generates the model 11, 101 of the patient specific cut guide instrument 10, 100. As observed in FIGS. 1-29, the instrument 10,100 has a body supporting a cut guide with the cut slot 15. The cut guide is used with a cutting tool, such as a saw, to perform a depth cut in the donor bone, the depth cut being positioned and oriented as a function of the contact of the body with the abutment on the donor bone, of the model 201 of the graft, and of the guide axis (axes). One or more guide channels are part of the body for alignment with the guide axis (axes). One or more anchor guides, such as the pin guides 15A, are located in the body of the instrument 10, 100 for securing the patient specific instrument cut guide 10, 100 on the donor bone as abutted with the abutment and aligned with the guide axis. The instrument body generator module 205 may also create other patient specific instruments, such as the barrel 130. The generator 205 outputs a model(s) 11, 101, in any appropriate format, such as non-transient instructions to machine the instrument 10, 100, a 3D printing file, etc.

In the system 200, the patient-specific instrument generator 203 may also have a tool selector module 206. The module 206 may identify the various bone-altering tools, such as 30, 40, 70, 120, etc (concurrently as 210) to be used for resurfacing the donor bone, harvesting the graft, etc. The module 206 may also provide data such as depth of penetration in the case of the bell saw 70.

The invention claimed is:

1. A method for harvesting a graft having at least an implant interface surface, a bone interface surface, and a planned spatial geometry therebetween, the method comprising:

obtaining a cut guide instrument specific to a patient's anatomy;

resurfacing an exposed surface of a donor bone by installing a guide rod on the donor bone and moving a resurfacing tool on the guide rod to form one of the implant interface surface and the bone interface surface of the graft;

securing the cut guide instrument to the bone relative to the resurfaced exposed surface by sliding the cut guide instrument along the guide rod and into abutment with the exposed surface;

performing a depth cut in the donor bone to form the other of the implant interface surface and the bone interface surface of the graft with the planned spatial geometry; and harvesting the graft from the donor bone.

2. The method according to claim 1, wherein resurfacing the exposed surface of the donor bone comprises resurfacing the exposed surface to form a planar surface used as the implant interface surface.

3. The method according to claim 2, wherein performing the depth cut comprises forming the bone interface surface into another planar surface, the exposed surface being non parallel to the bone interface surface.

4. The method according to claim 3, wherein harvesting the graft comprises forming a cylindrical body between the implant interface surface and the bone interface surface, an axis of the cylindrical body being normal to the implant interface surface.

5. The method according to claim 2, wherein harvesting the bone comprises securing an implant against the implant interface surface and removing the implant and graft from the donor bone.

6. The method according to claim 1, wherein harvesting the graft comprises harvesting the graft to obtain the spatial geometry based on one of a Walch glenoid indication and a Favard glenoid indication in a reverse shoulder arthroplasty.

7. The method according to claim 1, wherein harvesting the graft comprises harvesting the graft from a humerus being the donor bone, and further comprising implanting the graft and an implant onto a glenoid in a reverse shoulder arthroplasty.

8. The method according to claim 1, further comprising implanting the graft onto a recipient bone without further alterations to the graft after said harvesting from the donor bone.

9. The method according to claim 1, further comprising forming a peg bore in the graft, the peg bore being coaxial with a hole in the donor bone made by insertion of the guide rod.

10. The method according to claim 9, wherein forming the peg bore includes removing the guide rod.

11. The method according to claim 1, wherein resurfacing the exposed surface of the donor bone comprises resurfacing the exposed surface to form a spherical surface portion used as the bone interface surface.

12. The method according to claim 11, wherein performing the depth cut comprises forming the implant interface surface into a planar surface.

13. The method according to claim 12, wherein harvesting the graft comprises forming a cylindrical body between the implant interface surface and the bone interface surface, an axis of the cylindrical body being normal to the implant interface surface.

14. The method according to claim 11, wherein harvesting the graft comprises installing a second guide rod with a second guide channel of the cut guide instrument on the donor bone and sliding an instrument on the second guide rod.

15. The method according to claim 14, wherein harvesting the graft comprises forming a peg bore in the graft, the peg bore being coaxial with a hole in the donor bone made by insertion of the second guide rod.

16. The method according to claim 15, wherein forming the peg bore is removing the second guide rod.

17. The method according to claim 15, further comprising using a patient specific alignment instrument having a receptacle receiving and conforming to the bone interface surface and a hole in the receptacle receiving and aligned with the peg bore to install the implant onto the graft.

18. The method according to claim 17, wherein using the patient specific alignment instrument further comprises sliding the patient specific alignment instrument along a guide pin to position and impact the implant and graft on the recipient bone.

19. The method according to claim 1, wherein harvesting the graft comprises harvesting a cadaver allograft.

20. A method for harvesting a graft having at least an implant interface surface, a bone interface surface, and a planned spatial geometry therebetween, the method comprising:

obtaining a cut guide instrument specific to a patient's anatomy and having the planned spatial geometry between the implant interface surface and the bone interface surface based on a Walch glenoid indication and a Favard glenoid indication in a reverse shoulder arthroplasty;

resurfacing an exposed surface of a donor bone to form one of the implant interface surface and the bone interface surface of the graft;

securing the cut guide instrument to the bone relative to the resurfaced exposed surface;

performing a depth cut in the donor bone to form the other of the implant interface surface and the bone interface surface of the graft with the planned spatial geometry; and harvesting the graft from the donor bone to obtain the spatial geometry based on the one of the Walch glenoid indication and the Favard glenoid indication in the reverse shoulder arthroplasty.

21. The method according to claim 20, wherein resurfacing the exposed surface of the donor bone comprises resurfacing the exposed surface to form a planar surface used as the implant interface surface.

22. The method according to claim 21, wherein performing the depth cut comprises forming the bone interface surface into another planar surface, the exposed surface being non parallel to the bone interface surface.

23. The method according to claim 22, wherein harvesting the graft comprises forming a cylindrical body between the implant interface surface and the bone interface surface, an axis of the cylindrical body being normal to the implant interface surface.

24. The method according to claim 21, wherein harvesting the bone comprises securing an implant against the implant interface surface and removing the implant and graft from the donor bone.

25. The method according to claim 20, wherein harvesting the graft comprises harvesting the graft from a humerus being the donor bone, and further comprising implanting the graft and an implant onto a glenoid in a reverse shoulder arthroplasty.

26. The method according to claim 20, further comprising implanting the graft onto a recipient bone without further alterations to the graft after said harvesting from the donor bone.

27. The method according to claim 20, further comprising forming a peg bore in the graft, the peg bore being coaxial with a hole in the donor bone made by insertion of the guide rod.

28. The method according to claim 27, wherein forming the peg bore includes removing the guide rod.

29. A method for harvesting a graft having at least an implant interface surface, a bone interface surface, and a planned spatial geometry therebetween, the method comprising:

obtaining a cut guide instrument specific to a patient's anatomy;

resurfacing an exposed surface of a donor bone to form a planar surface used as the implant interface surface;

securing the cut guide instrument to the bone relative to the resurfaced exposed surface;

performing a depth cut in the donor bone to form the bone interface surface of the graft with the planned spatial geometry; and harvesting the graft from the donor bone by securing an implant against the implant interface surface and removing the implant and graft from the donor bone.

30. The method according to claim 29, wherein performing the depth cut comprises forming the bone interface surface into another planar surface, the exposed surface being non parallel to the bone interface surface.

31. The method according to claim 30, wherein harvesting the graft comprises forming a cylindrical body between the implant interface surface and the bone interface surface, an axis of the cylindrical body being normal to the implant interface surface.

32. The method according to claim 29, wherein harvesting the graft comprises harvesting the graft from a humerus being the donor bone, and further comprising implanting the graft and an implant onto a glenoid in a reverse shoulder arthroplasty.

33. The method according to claim 29, further comprising implanting the graft onto a recipient bone without further alterations to the graft after said harvesting from the donor bone.

34. The method according to claim 29, further comprising forming a peg bore in the graft, the peg bore being coaxial with a hole in the donor bone made by insertion of the guide rod.

35. The method according to claim 34, wherein forming the peg bore includes removing the guide rod.

36. A method for harvesting a graft having at least an implant interface surface, a bone interface surface, and a planned spatial geometry therebetween, the method comprising:
obtaining a cut guide instrument specific to a patient's anatomy;
resurfacing an exposed surface of a donor bone to form a spherical surface portion used as the bone interface surface;
securing the cut guide instrument to the bone relative to the resurfaced exposed surface;
performing a depth cut in the donor bone to form the implant interface surface into a planar surface of the graft with the planned spatial geometry; and
harvesting the graft from the donor bone.

37. The method according to claim 36, wherein harvesting the graft comprises forming a cylindrical body between the implant interface surface and the bone interface surface, an axis of the cylindrical body being normal to the implant interface surface.

38. The method according to claim 36, wherein harvesting the graft comprises installing a second guide rod with a second guide channel of the cut guide instrument on the donor bone and sliding an instrument on the second guide rod.

39. The method according to claim 38, wherein harvesting the graft comprises forming a peg bore in the graft, the peg bore being coaxial with a hole in the donor bone made by insertion of the second guide rod.

40. The method according to claim 39, wherein forming the peg bore is removing the second guide rod.

41. The method according to claim 39, further comprising using a patient specific alignment instrument having a receptacle receiving and conforming to the bone interface surface and a hole in the receptacle receiving and aligned with the peg bore to install the implant onto the graft.

42. The method according to claim 41, wherein using the patient specific alignment instrument further comprises sliding the patient specific alignment instrument along a guide pin to position and impact the implant and graft on the recipient bone.

* * * * *